(12) United States Patent
Wolfman et al.

(10) Patent No.: US 7,202,210 B2
(45) Date of Patent: Apr. 10, 2007

(54) MODIFIED AND STABILIZED GDF PROPEPTIDES AND USES THEREOF

(75) Inventors: Neil M. Wolfman, Dover, MA (US); Soo-Peang Khor, Saratoga, CA (US); Kathleen N. Tomkinson, Cambridge, MA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/071,499

(22) Filed: Feb. 8, 2002

(65) Prior Publication Data

US 2003/0104406 A1 Jun. 5, 2003

Related U.S. Application Data

(60) Provisional application No. 60/267,509, filed on Feb. 8, 2001.

(51) Int. Cl.
  *C12Q 1/68* (2006.01)
  *C07H 21/04* (2006.01)
  *C12P 21/02* (2006.01)
  *C12N 5/06* (2006.01)
  *C07K 14/475* (2006.01)

(52) U.S. Cl. ............... 514/12; 435/6; 435/69.4; 435/320.1; 435/325; 530/399

(58) Field of Classification Search ............ 530/324, 530/350; 519/2; 435/7.1
  See application file for complete search history.

(56) References Cited

U.S. PATENT DOCUMENTS

| | | | | |
|---|---|---|---|---|
| 4,179,337 A | * | 12/1979 | Davis et al. | 435/181 |
| 5,116,944 A | * | 5/1992 | Sivam et al. | 530/362 |
| 5,350,836 A | * | 9/1994 | Kopchick et al. | 530/399 |
| 5,639,638 A | | 6/1997 | Wozney et al. | |
| 5,700,911 A | | 12/1997 | Wozney et al. | |
| 5,723,125 A | * | 3/1998 | Chang et al. | 424/134.1 |

(Continued)

FOREIGN PATENT DOCUMENTS

EP  1 061 940 B1  12/2003

(Continued)

OTHER PUBLICATIONS

Thies et al. "GDF-8 Propeptide Binds to GDF-8 and Antagonizes Biological Activity by Inhibiting GDF-8 Receptor Binding" Growth Factors, 18:251-259 (Nov./Dec. 2001)—Correction of citation from 1449 filed on Jun. 24, 2005.*

(Continued)

*Primary Examiner*—Marianne P. Allen
*Assistant Examiner*—Cherie Woodward
(74) *Attorney, Agent, or Firm*—Finnegan, Henderson, Farabow, Garrett & Dunner, L.L.P.

(57) ABSTRACT

Modified and stabilized propeptides of Growth Differentiation Factor proteins, such as GDF-8 and Bone Morphogenetic Protein-11, are disclosed. Also disclosed are methods for making and using the modified propeptides to prevent or treat human or animal disorders in which an increase in muscle tissue would be therapeutically beneficial. Such disorders include muscle or neuromuscular disorders (such as amyotrophic lateral sclerosis, muscular dystrophy, muscle atrophy, congestive obstructive pulmonary disease, muscle wasting syndrome, sarcopenia, or cachexia), metabolic diseases or disorders (such as such as type 2 diabetes, noninsulin-dependent diabetes mellitus, hyperglycemia, or obesity), adipose tissue disorders (such as obesity), and bone degenerative diseases (such as osteoporosis).

20 Claims, 22 Drawing Sheets

U.S. PATENT DOCUMENTS

| | | | |
|---|---|---|---|
| 5,756,457 | A | 5/1998 | Wang et al. |
| 5,827,733 | A | 10/1998 | Lee et al. |
| 5,914,234 | A | 6/1999 | Lee et al. |
| 5,994,618 | A | 11/1999 | Lee et al. |
| 6,004,937 | A | 12/1999 | Wood et al. |
| 6,096,506 | A | 8/2000 | Lee et al. |
| 6,340,668 | B1 | 1/2002 | Celeste et al. |
| 6,368,597 | B1 | 4/2002 | Strassmann et al. |
| 6,369,201 | B1 | 4/2002 | Barker et al. |
| 6,437,111 | B1 | 8/2002 | Wozney et al. |
| 6,656,475 | B1 | 12/2003 | Lee et al. |
| 6,696,260 | B1 | 2/2004 | Lee et al. |
| 6,835,544 | B2 | 12/2004 | Mathews et al. |
| 2002/0150577 | A1 | 10/2002 | Lee et al. |
| 2003/0138422 | A1 | 7/2003 | Aghajanian et al. |
| 2003/0162714 | A1 | 8/2003 | Hill et al. |
| 2003/0180306 | A1 | 9/2003 | Hill et al. |
| 2004/0077053 | A1 | 4/2004 | Lee et al. |
| 2004/0138118 | A1 | 7/2004 | Wolfman et al. |
| 2004/0142382 | A1 | 7/2004 | Veldman et al. |
| 2004/0181033 | A1 | 9/2004 | Han et al. |
| 2004/0223966 | A1 | 11/2004 | Wolfman et al. |
| 2005/0043232 | A1 | 2/2005 | Lee et al. |

FOREIGN PATENT DOCUMENTS

| | | |
|---|---|---|
| EP | 1 444 985 A1 | 8/2004 |
| WO | WO 94-21681 | 9/1994 |
| WO | WO 94-26892 | 11/1994 |
| WO | WO 96-01845 | 1/1996 |
| WO | WO 99/24058 | 5/1999 |
| WO | WO 99/45949 | 9/1999 |
| WO | WO 99/56768 | 11/1999 |
| WO | WO 00/11163 | 3/2000 |
| WO | WO 00/43781 | 7/2000 |
| WO | WO 01-64888 A2 | 9/2001 |
| WO | WO 02/09641 A2 | 2/2002 |
| WO | WO 03-027248 | 4/2003 |
| WO | WO 2004/058988 A2 | 7/2004 |

OTHER PUBLICATIONS

Zwijsen et al., "Characterization of a Rat C6 Glioma-Secreted Follistatin-Related Protein (FRP) Cloning and Sequence of the Human Homologue" Eur J. Biochem. 225: 937-946 (1994)—Correction of citation from 1449 filed on Jun. 24, 2005.*
Bowie et al, 1990, Science 247:1306-1310.*
Wells, 1990, Biochemistry 29:8509-8517.*
Skolnick et al. 2000, Trends in Biotech. 18:34-39.*
Bork . 2000, Genome Research 10:398-400.*
Doerks et al. 1998, Trends in Genetics 14:248-250.*
Vukicevic et al. 1996, PNAS USA 93:9021-9026.*
Massague, 1987, Cell 49:437-8.*
Pilbeam et al., 1993, Bone 14:717-720.*
Partial International Search Report for International Application No. PCT/US02/03467, mailed Dec. 6, 2002.
Hamrick et al., "Bone Mineral Content and Density in the Humerus of Adult Myostatin-Deficient Mice" *Calcified Tissue International*, 71(1):63-68 (2002).
Lee et al., "Regulation of Myostatin Activity and Muscle Growth" *PNAS*, 98(16):9306-9311 (2001).
Zhu et al., "Dominant Negative Myostatin Produces Hypertrophy Without Hyperplasia in Muscle" *FEBS Letters*, 474:71-75 (2000).
McPherron et al. "Double Muscling in Cattle Due to Mutations in the Myostatin Gene" *PNAS*, 94:12457-12461 (Nov. 1997).
Thies et al. "GDF-8 Propeptide Binds to GDF-8 and Antagonizes Biological Activity by Inhibiting GDF-8 Receptor Binding" *Growth Factors*, 18:251-259 (2000).
Jiang, et al., "Characterization and Identification of the Inhibitory Domain of GDF-8 Propeptide," *Biochem. Biophys. Res.* 315:525-531 (2004).
Alexander et al., "Human Parathyroid Hormone 1-34 Reverses Bone Loss In Ovariectomized Mice," *J. Bone Miner. Res.* 16:1665-1673 (2001).
Alliel et al., "Testican, a Multidomain Testicular Proteoglycan Resembling Modulators of Cell Social Behaviour," *Eur. J. Biochem.* 214:347-350 (1993).
Amthor et al., "The Expression and Regulation of Follistatin and a Follistatin-like Gene During Avian Somite Compartmentalization and Myogenesis," *Dev. Biol.* 178:343-362 (1996).
Andersson et al., "Repeated *In Vivo* Determinations of Bone Mineral Density During Parathyroid Hormone Treatment in Ovariectomized Mice," *J. Endocrinol.* 170:529-537 (2001).
Ashmore et al., "Comparative Aspects of Muscle Fiber Types in Fetuses of the Normal and "Double-Muscled" Cattle," *Growth* 38:501-506 (1974).
Attisano et al., "Activation of Signalling by the Activin Receptor Complex," *Mol. Cell. Biol.* 16:1066-1073 (1996).
Bakker et al., Duchenne and Becker Muscular Dystrophies. In *Diagnostic Criteria for Neuromuscular Disorders*, 2nd ed., Emery, ed., Royal Society of Medicine Press, 1998; pp. 1-4.
Bartholin et al., "FLRG, an Activin-Binding Protein, is a New Target of TGFβ Transcription Activation Through Smad Proteins," *Oncogene* 20:5409-5419 (2001).
Blader et al., "Cleavage of the BMP-4 Antagonist Chordin by Zebrafish Tolloid," *Science* 278:1937-1940 (1997).
Bogdanovich et al., "Functional Improvement of Dystrophic Muscle by Myostatin Blockade," *Nature* 420:418-421 (2002).
Brown et al., "Physicochemical Activation of Recombinant Latent Transforming Growth Factor-beta's 1, 2, and 3," *Growth Factors* 3:35-43 (1990).
Bulfield et al., "X Chromosome-Linked Muscular Dystrophy (*mdx*) in the Mouse," *Proc. Natl. Acad. Sci. U.S.A.* 81:1189-1192 (1984).
D'Angelo et al., "Authentic Matrix Vesicles Contain Active Metalloproteases (MMP)," *J. Biol. Chem.* 276:11347-11353 (2001).
Derynck et al., "Human Transforming Growth Factor-β Complementary DNA Sequence and Expression in Normal and Transformed Cells," *Nature* 316:701-705 (1985).
Donoghue et al., "Rostrocaudal Gradient of Transgene Expression in Adult Skeletal Muscle," *Proc. Natl. Acad. Sci. U.S.A.* 88:5846-5851 (1991).
Emery, "The Muscular Dystrophies," *Lancet* 359:687-695 (2002).
Escolar et al., "Pharmacologic and Genetic Therapy for Childhood Muscular Dystrophies," *Current Neurology and Neuroscience Reports* 1:168-174 (2001).
Gamer et al., "A Novel BMP Expressed in Developing Mouse Limb, Spinal Cord, and Tail Bud Is a Potent Mesoderm Inducer in *Xenopus* Embryos," *Dev. Biol.* 208:222-232 (1999).
Gamer et al., "Gdf11 is a Negative Regulator of Chondrogenesis and Myogenesis in the Developing Chick Limb," *Dev. Biol.* 229:407-420 (2001).
Gentry et al., "The Pro Domain of Pre-Pro-Transforming Growth Factor β1 When Independently Expressed is a Functional Binding Protein for the Mature Growth Factor," *Biochemistry* 29:6851-6857 (1990).
Gillis, "Multivariate Evaluation of the Functional Recovery Obtained by the Overexpression of Utrophin in Skeletal Muscles of the *mdx* Mouse," *Neuromuscular Disorders* 12:S90-S94 (2002).
Gonzalez-Cadavid et al., "Organization of the Human Myostatin Gene and Expression in Healthy Men and HIV-Infected Men With Muscle Wasting," *Proc. Natl. Acad. Sci. U.S.A.* 95:14938-14943 (1998).
Grady et al., "Skeletal and Cardiac Myopathies in Mice Lacking Utrophin and Dystrophin: A Model for Duchenne Muscular Dystropy," *Cell* 90:729-738 (1997).
Granchelli et al., "Pre-Clinical Screening of Drugs Using the *mdx* Mouse," *Neuromuscular Disorders* 10:235-239 (2000).
Hamrick et al., "Femoral Morphology and Cross-Sectional Geometry of Adult Myostatin-Deficient Mice," *Bone* 27:343-349 (2000).
Hayette et al., "FLRG (Follistatin-Related Gene), A New Target of Chromosomal Rearrangement in Malignant Blood Disorders," *Oncogene* 16:2949-2954 (1998).

Hill et al., "Regulation of Myostatin in Vivo by Growth and Differentiation Factor-Associated Serum Protein-1: A Novel Protein with Protease Inhibitor and Follistatin Domains," *Mol. Endocrinol.* 17:1144-1154 (2003).

Hill et al., "The Myostatin Propeptide and the Follistatin-Related Gene Are Inhibitory Binding Proteins of Myostatin in Normal Serum," *J. Biol. Chem.* 277:40735-40741 (2002).

Hoffman et al., "Conservation of the Duchenne Muscular Dystrophy Gene in Mice and Humans," *Science* 238:347-350 (1987).

Hoodless et al., "Mechanisms and Function of Signaling by the TGFβ Superfamily," *Curr. Top. Microbiol. Immunol.* 228:236-272 (1998).

Huet et al., "Skeletal Muscle Cell Hypertrophy Induced by Inhibitors of Metalloproteases; Myostatin as a Potential Mediator," *Am. J. Physiol. Cell. Physiol.* 281:C1624-C1634 (2001).

Kambadur et al., "Mutations in myostatin (GDF8) In Double-Muscled Belgian Blue and Piedmontese Cattle," *Genome Res.* 7:910-915 (1997).

Kato, "A Secreted Tumor-Suppressor, mac25, with Activin-Binding Activity," *Mol. Med.* 6:126-135 (2000).

Kessler et al., "Bone Morphogenetic Protein-1: The Type I Procollagen C-Proteinase," *Science* 271:360-362 (1996).

Khurana et al., "Pharmacological Strategies for Muscular Dystrophy," *Nature Rev. Drug Disc.* 2:379-386 (2003).

Kim et al., "Inhibition of Preadipocyte Differentiation by Myostatin Treatment in 3T3-L1 Cultures," *Biochem. Biophys. Res. Commun.* 281:902-906 (2001).

Kingsley, D.M., "The TGF-β Superfamily: New Members, New Receptors, and New Genetic Tests of Function in Different Organisms," *Genes Dev.* 8:133-146 (1994).

Lang et al., "Regulation of Myostatin by Glucocorticoids After Thermal Injury," *FASEB J.* 15:1807-1809 (2001).

Lee et al., "Analysis of Site-Directed Mutations in Human Pro-α2(1) Collagen Which Block Cleavage by the C-Proteinase," *J. Biol. Chem.* 265:21992-21996 (1990).

Li et al., "The C-Proteinase that Processes Procollagens to Fibrillar Collagens is Identical to the Protein Previously Identified as Bone Morphogenic Protein-1," *Proc. Natl. Acad. Sci. U.S.A.* 93:5127-5130 (1996).

Lin et al., "Expression Cloning of the TGF-β Type II Receptor, a Functional Transmembrane Serine/Threonine Kinase," *Cell* 68:775-785 (1992).

Liu et al., "Assigning the Positional Identity of Spinal Motor Neurons: Rostrocaudal Patterning of Hox-c Expression by FGFs, Gdf11, and Retinoids," *Neuron* 32:997-1012 (2001).

Lyons et al., "Proteolytic Activation of Latent Transforming Growth Factor-β from Fibroblast-Conditioned Medium," *J. Cell Biol.* 106:1659-1665 (1988).

Maeda et al., "Activation of Latent Transforming Growth Factor β1 by Stromelysin 1 in Extracts of Growth Plate Chondrocyte-Derived Matrix Vesicles," *J. Bone Miner. Res.* 16:1281-1290 (2001).

Maguer-Satta et al., "During Hematopoiesis, Expression of FLRG, a Novel Activin A Ligand, is regulated by TGF-β," *Exp. Hematol.* 29:301-308 (2001).

Marques et al., "Production of a DPP Activity Gradient in the Early Drosophilia Embryo through the Opposing Actions of the SOG and TLD Proteins," *Cell* 91:417-426 (1997).

Massagué et al., "Receptors for the TGF-β Family," *Cell* 69:1067-1070 (1992).

Massagué et al., "The TGF-β Family and its Composite Receptors," *Trends Cell Biol.* 4:172-178 (1994).

Massagué, "How Cells Read TGF-β Signals," *Nature Rev. Mol. Cell. Biol.* 1:169-178 (2000).

Massagué, "The Transforming Growth Factor-β Family," *Annu. Rev. Cell Biol.* 6:597-641 (1990).

Matsuda et al., "Visualization of Dystrophic Muscle Fibers in Mdx Mouse by Vital Staining with Evans Blue: Evidence of Apoptosis in Dystrophin-Deficient Muscle," *J. Biochem.* 118:959-964 (1995).

McPherron et al., "Regulation of Skeletal Muscle Mass in Mice by a New TGF-β Superfamily Member," *Nature* 387:83-90 (1997).

McPherron et al., "Suppression of Body Fat Accumulation in Myostatin-Deficient Mice," *J. Clin. Invest.* 109:595-601 (2002).

McPherron et al., "Regulation of Anterior/Posterior Patterning of the Axial Skeleton by Growth/Differentiation Factor 11," *Nature Genet.* 22:260-264 (1999).

Miyazono et al., "Latent High Molecular Weight Complex of Transforming Growth Factor β1," *J. Biol. Chem.* 263:6407-6415 (1988).

Morrison et al., "T-Cell-Dependent Fibrosis in the mdx Dystrophic Mouse," *Lab. Invest.* 80:881-891 (2000).

Motamed, "Moleclues in Focus, SPARC (Osteonectin/BM-40)," *Int. J. Biochem. Cell Biol.* 31:1363-1366 (1999).

Moustakas et al., "Smad Regulation in TGF-β Signal Transduction," *J. Cell Sci.* 114:4359-4369 (2001).

Nakamura et al., "Follistatin, an Activin-Binding Protein, Associates with Heparan Sulfate Chains of Proteoglycans on Follicular Granulosa Cells," *J. Biol. Chem.* 266:19432-19437 (1991).

Nakamura et al., "Isolation and Characterization of Activin Receptor from Mouse Embryonal Carcinoma Cells," *J. Biol. Chem.* 267:18924-18928 (1992).

Nakashima et al., "Expression of Growth/Differentiation Factor 11, A New Member of the BMP/TGF β Superfamily During Mouse Embryogenesis," *Mech. Dev.* 80:185-189 (1999).

Ngo et al., In *The Protein Folding Problems and Tertiary Structure Prediction*, Merz et al., eds., *Brickhauser*, Springer Verlag, Boston, pp. 433-434 & 492-495 (1994).

Pappano et al., "Use of BMP1-TII1 Doubly Homozygous Null Mice and Proteomics to Identify and Validate In Vivo Substrates of Bone Morphogenetic Protein 1/Tolloid-Like Metalloproteinases," *Mol. Cell. Biol.* 23:4428-4438 (2003).

Patel et al., "Cloning and Early Dorsal Axial Expression of Flik, a Chick Follistatin-Related Gene: Evidence for Involvement in Dorsalization-Neural Induction," *Dev. Biol.* 178:327-342 (1996).

Patthy et al., "Functions of Agrin and Agrin-Related Proteins," *Trends Neurosci.* 16:76-81 (1993).

Phillips et al., "Follistatin: A Multifunctional Regulatory Protein," *Front. Neuroendocrin.* 19:287-322 (1998).

Piccolo et al., "Cleavage of Chordin by Xolloid Metalloprotease Suggests a Role for Proteolytic Processing in the Regulation of Spemann Organizer Activity," *Cell* 91:407-416 (1997).

R&D Systems, Inc., "Recombinant Human Activin Receptor IIB-Fc Chimera: Specifications and Use," Cat. No. 339-RB (2002).

Riley et al., "The Use of Single Nucleotide Polymorphisms in the Isolation of Common Disease Genes," *Pharmacogenomics* 1:39-47 (2000).

Sato et al., "Inhibition of Endothelial Cell Movement by Pericytes and Smooth Muscle Cells: Activation of a Latent Transforming Growth Factor-β1-Like Molecule by Plasmin During Co-Culture," *J. Cell Biol.* 109:309-315 (1989).

Schäcke et al., "Mechanisms Involved in the Side Effects of Glucocorticoids," *Pharmacol. Ther.* 96:23-43 (2002).

Schneyer et al., "Follistatin-Related Protein (FSRP): A New Member of the Follistatin Gene Family," *Mol. Cell. Endocrinol.* 180:33-38 (2001).

Scott et al., "Bone Morphogenetic Protein-1 Processes Probiglycan," *J. Biol. Chem.* 275:30504-30511 (2000).

Scott et al., "Mammalian BMP-1-Tolloid-Related Metalloproteinases, Including Novel Family Member Mammalian Tolloid-Like 2, Have Differential Enzymatic Activities and Distributions of Expression Relevant to Patterning and Skeletogeneses," *Dev. Biol.* 213:283-300 (1999).

Shibanuma et al., "Cloning From a Mouse Osteoblastic Cell Line of a Set of Transforming-Growth-Factor-β1-Regulated Genes, One of Which Seems to Encode a Follistatin-Related Polypeptide," *Eur. J. Biochem.* 217:13-19 (1993).

Sternberg et al., "Identification of Upstream and Intragenic Regulator Elements that Confer Cell-Type-Restricted and Differentiation-Specific Expression on the Muscle Creatine Kinase Gene," *Mol. Cell. Biol.* 8:2896-2909 (1988).

Swatland et al., "Fetal Development of the Double Muscled Condition in Cattle," *J. Anim. Sci.* 38:752-757 (1974).

Takahara et al., "Bone Morphogenetic Protein-1 and a Mammalian Tolloid Homologue (mTld) Are Encoded by Alternatively Spliced Transcripts Which Are Differentially Expressed in Some Tissues," *J. Biol. Chem.* 269:32572-32578 (1994).

Takahara et al., "Characterization of a Novel Gene Product (Mammalian Tolloid-like) with High Sequence Similarity to Mammalian Tolloid/Bone Morphogenetic Protein-1," *Genomics* 34:157-165 (1996).

Torres et al., "The Mutant mdx: Inherited Myopathy in the Mouse," *Brain* 110:269-299 (1987).

Trexler et al., "Distinct Expression Pattern of Two Related Human Proteins Containing Multiple Types of Protease-Inhibitory Modules," *Biol. Chem.* 383:223-228 (2002).

Trexler et al., "A Human Protein Containing Multiple Types of Protease-Inhibitory Modules," *Proc. Natl. Acad. Sci. U.S.A.* 98:3705-3709 (2001).

Tsuchida et al., "Identification and Characterization of a Novel Follistatin-like Protein as a Binding Protein for the TGF-β Family," *J. Biol. Chem.* 275:40788-40796 (2000).

Tsuchida et al., "Intracellular and Extracellular Control of Activin Function by Novel Regulatory Molecules," *Mol. Cell. Endocrinol.* 180:25-31 (2001).

Umland et al., "Review of the Molecular and Cellular Mechanisms of Action of Glucocorticoids for Use in Asthma," *Pulmonary Pharmacology & Therapeutics* 15:35-50 (2002).

Uzel et al., "Multiple Bone Morphogenetic Protein 1-Related Mammalian Metalloproteinases Process Pro-Lysyl Oxidase at the Correct Physiological Site and Control Lysyl Oxidase Activation in Mouse Embryo Fibroblast Cultures," *J. Biol. Chem.* 276:22537-22543 (2001).

Wagner et al., "Loss of Myostatin Attenuates Severity of Muscular Dystrophy in mdx Mice," *Ann. Neurol.* 52:832-836 (2002).

Wakefield et al., "Latent Transforming Growth Factor-β From Human Platelets," *J. Biol. Chem.* 263:7646-7654 (1988).

Whittemore et al., "Inhibition of Myostatin in Adult Mice Increases Skeletal Muscle Mass and Strength," *Biochem. Biophys. Res. Commun.* 300:965-971 (2003).

Wolfman et al., "Activation of Latent Myostatin by the BMP-1/Tolloid Family of Metalloproteinases," *Proc. Natl. Acad. Sci. U.S.A.* 100:15842-15846 (2003).

Wu et al., "Autoregulation of Neurogenesis by GDF-11," *Neuron* 37:197-207 (2003).

Wuytens et al., "Identification of Two Amino Acids in Activin A That Are Important for Biological Activity and Binding to the Activin Type II Receptors," *J. Biol. Chem.* 274:9821-9827 (1999).

Yu et al., "Cell Surface-Localized Matrix Metalloproteinase-9 Proteolytically Activates TGF-β and Promotes Tumor Invasion and Angiogenesis," *Genes Dev.* 14:163-176.

Zimmers et al., "Induction of Cachexia in Mice by Systematically Administered Myostatin," *Science* 296:1486-1488 (2002).

Zwusen et al., "Characterization of a Rat $C_6$ Glioma-Secreted Follistain-Related Protein (FRP) Cloning and Sequence of the Human Homologue," *Eur. J. Biochem.* 225:937-946 (1994).

\* cited by examiner

| NEGS | | PKRS | EPRG | | |
|---|---|---|---|---|---|
| | Secretory leader | Mu GDF-8 propeptide | | Mu IgG2a Fc | PGK |

SEQ ID No:20
MMQKLQMYVYIYLFMLIAAGPVDLNEGSEREENVEKEGLCNACAWRQNTRYSRIEAIKIQILSKLRLET
APNISKDAIRQLLPRAPPLRELIDQYDVQRDDSSDGSLEDDDYHATTETIITMPTESDFLMQADGKPKC
CFFKFSSKIQYNKVVKAQLWIYLRPVKTPTTVFVQILRLIKPMKDGTRYTGIRSLKLDMSPGTGIWQSI
DVKTVLQNWLKQPESNLGIEIKALDENGHDLAVTFPGPGEDGLNPFLEVKVTDTPKRSEPRGPTIKPCP
PCKCPAPNLEGGPSVFIFPPKIKDVLMISLSPIVTCVVVDVSEDDPDVQISWFVNNVEVHTAQTQTHRE
DYNSTLRVVSALPIQHQDWMSGKAFACAVNNKDLPAPIERTISKPKGSVRAPQVYVLPPPEEEMTKKQV
TLTCMVTDFMPEDIYVEWTNNGKTELNYKNTEPVLDSDGSYFMYSKLRVEKKNWVERNSYSCSVVHEGL
HNHHTTKSFSRTPGK

Fig. 7A

| NEGS | | PKRS | GSGS | EPRG | | |
|---|---|---|---|---|---|---|
| | Secretory leader | Mu GDF-8 propeptide | | | Mu IgG2a Fc | PGK |

SEQ ID No:21
MMQKLQMYVYIYLFMLIAAGPVDLNEGSEREENVEKEGLCNACAWRQNTRYSRIEAIKIQILSKLRLET
APNISKDAIRQLLPRAPPLRELIDQYDVQRDDSSDGSLEDDDYHATTETIITMPTESDFLMQADGKPKC
CFFKFSSKIQYNKVVKAQLWIYLRPVKTPTTVFVQILRLIKPMKDGTRYTGIRSLKLDMSPGTGIWQSI
DVKTVLQNWLKQPESNLGIEIKALDENGHDLAVTFPGPGEDGLNPFLEVKVTDTPKRSGSGSEPRGPTI
KPCPPCKCPAPNLEGGPSVFIFPPKIKDVLMISLSPIVTCVVVDVSEDDPDVQISWFVNNVEVHTAQTQ
THREDYNSTLRVVSALPIQHQDWMSGKAFACAVNNKDLPAPIERTISKPKGSVRAPQVYVLPPPEEEMT
KKQVTLTCMVTDFMPEDIYVEWTNNGKTELNYKNTEPVLDSDGSYFMYSKLRVEKKNWVERNSYSCSVV
HEGLHNHHTTKSFSRTPGK

Fig. 7B

| NENS | PKRS | EPKS | | PGK |
|---|---|---|---|---|
| Secretory leader | Hu GDF-8 propeptide | | Hu IgG1 Fc | |

SEQ ID No:22

MQKLQLCVYIYLFMLIVAGPVDLNENSEQKENVEKEGLCNACTWRQNTKSSRIEAIKIQILSKLRLETAPN
ISKDVIRQLLPKAPPLRELIDQYDVQRDDSSDGSLEDDDYHATTETIITMPTESDFLMQVDGKPKCCFFKF
SSKIQYNKVVKAQLWIYLRPVETPTTVFVQILRLIKPMKDGTRYTGIRSLKLDMNPGTGIWQSIDVKTVLQ
NWLKQPESNLGIEIKALDENGHDLAVTFPGPGEDGLNPFLEVKVTDTPKRSEPKSCDKTHTCPPCPAPELL
GGPSVFLFPPKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSLSLSPGK

Fig. 11A

| NENS | PKRS | DKT | | |
|---|---|---|---|---|
| Secretory leader | Hu GDF-8 propeptide | | Hu IgG1 Fc mutated | PGK |

SEQ ID No: 23   MQKLQLCVYIYLFMLIVAGPVDLNENSEQKENVEKEGLCNACTWRQNTKSSRIEAIKIQILSKLRLETAPN
ISKDVIRQLLPKAPPLRELIDQYDVQRDDSSDGSLEDDDYHATTETIITMPTESDFLMQVDGKPKCCFFKF
SSKIQYNKVVKAQLWIYLRPVETPTTVFVQILRLIKPMKDGTRYTGIRSLKLDMNPGTGIWQSIDVKTVLQ
NWLKQPESNLGIEIKALDENGHDLAVTFPGPGEDGLNPFLEVKVTDTPKRSDKTHTCPPCPAPEALGAPSV
FLFPPKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHNHYTQKSLSLSPGK

SEQ ID NO:1 Human GDF-8 precursor protein - protein sequence

MQKLQLCVYIYLFMLIVAGPVDLNENSEQKENVEKEGLCNACTWRQNTKSS
RIEAIKIQILSKLRLETAPNISKDVIRQLLPKAPPLRELIDQYDVQRDDSS
DGSLEDDDYHATTETIITMPTESDFLMQVDGKPKCCFFKFSSKIQYNKVVK
AQLWIYLRPVETPTTVFVQILRLIKPMKDGTRYTGIRSLKLDMNPGTGIWQ
SIDVKTVLQNWLKQPESNLGIEIKALDENGHDLAVTFPGPGEDGLNPFLEV
KVTDTPKRSRRDFGLDCDEHSTESRCCRYPLTVDFEAFGWDWIIAPKRYKA
NYCSGECEFVFLQKYPHTHLVHQANPRGSAGPCCTPTKMSPINMLYFNGKE
QIIYGKIPAMVVDRCGCS

Fig. 14B

SEQ ID NO:2 Human GDF-8 precursor protein - DNA sequence

ATGCAAAAACTGCAACTCTGTGTTTATATTTACCTGTTTATGCTGATTGT
TGCTGGTCCAGTGGATCTAAATGAGAACAGTGAGCAAAAAGAAAATGTGG
AAAAAGAGGGGCTGTGTAATGCATGTACTTGGAGACAAAACACTAAATCT
TCAAGAATAGAAGCCATTAAGATACAAATCCTCAGTAAACTTCGTCTGGA
AACAGCTCCTAACATCAGCAAAGATGTTATAAGACAACTTTTACCCAAAG
CTCCTCCACTCCGGGAACTGATTGATCAGTATGATGTCCAGAGGGATGAC
AGCAGCGATGGCTCTTTGGAAGATGACGATTATCACGCTACAACGGAAAC
AATCATTACCATGCCTACAGAGTCTGATTTTCTAATGCAAGTGGATGGAA
AACCCAAATGTTGCTTCTTTAAATTTAGCTCTAAAATACAATACAATAAA
GTAGTAAAGGCCCAACTATGGATATATTTGAGACCCGTCGAGACTCCTAC
AACAGTGTTTGTGCAAATCCTGAGACTCATCAAACCTATGAAAGACGGTA
CAAGGTATACTGGAATCCGATCTCTGAAACTTGACATGAACCCAGGCACT
GGTATTTGGCAGAGCATTGATGTGAAGACAGTGTTGCAAAATTGGCTCAA
ACAACCTGAATCCAACTTAGGCATTGAAATAAAAGCTTTAGATGAGAATG
GTCATGATCTTGCTGTAACCTTCCAGGACCAGGAGAAGATGGGCTGAAT
CCGTTTTTAGAGGTCAAGGTAACAGACACACCAAAAAGATCCAGAAGGGA
TTTTGGTCTTGACTGTGATGAGCACTCAACAGAATCACGATGCTGTCGTT
ACCCTCTAACTGTGGATTTTGAAGCTTTTGGATGGGATTGGATTATCGCT
CCTAAAAGATATAAGGCCAATTACTGCTCTGGAGAGTGTGAATTTGTATT
TTTACAAAAATATCCTCATACTCATCTGGTACACCAAGCAAACCCCAGAG
GTTCAGCAGGCCCTTGCTGTACTCCCACAAAGATGTCTCCAATTAATATG
CTATATTTTAATGGCAAAGAACAAATAATATATGGGAAAATTCCAGCGAT
GGTAGTAGACCGCTGTGGGTGCTCA

Fig. 14C

SEQ ID NO:3 Human mature GDF-8 – protein sequence

DFGLDCDEHSTESRCCRYPLTVDFEAFGWDWIIAPKRYKANYCSGECEFVF
LQKYPHTHLVHQANPRGSAGPCCTPTKMSPINMLYFNGKEQIIYGKIPAMV
VDRCGCS

Fig. 14D

SEQ ID NO:4 Human mature GDF-8 – DNA sequence

GATTTTGGTCTTGACTGTGATGAGCACTCAACAGAATCACGATGCTGTCG
TTACCCTCTAACTGTGGATTTTGAAGCTTTTGGATGGGATTGGATTATCG
CTCCTAAAAGATATAAGGCCAATTACTGCTCTGGAGAGTGTGAATTTGTA
TTTTTACAAAAATATCCTCATACTCATCTGGTACACCAAGCAAACCCCAG
AGGTTCAGCAGGCCCTTGCTGTACTCCCACAAAGATGTCTCCAATTAATA
TGCTATATTTTAATGGCAAAGAACAAATAATATATGGGAAAATTCCAGCG
ATGGTAGTAGACCGCTGTGGGTGCTCA

Fig. 14E

SEQ ID NO:5 Human GDF-8 propeptide – protein sequence

NENSEQKENVEKEGLCNACTWRQNTKSSRIEAIKIQILSKLRLETAPNISK
DVIRQLLPKAPPLRELIDQYDVQRDDSSDGSLEDDDYHATTETIITMPTES
DFLMQVDGKPKCCFFKFSSKIQYNKVVKAQLWIYLRPVETPTTVFVQILRL
IKPMKDGTRYTGIRSLKLDMNPGTGIWQSIDVKTVLQNWLKQPESNLGIEI
KALDENGHDLAVTFPGPGEDGLNPFLEVKVTDTPKRSRR

Fig. 14F

SEQ ID NO:6 Human GDF-8 propeptide - DNA sequence

AATGAGAACAGTGAGCAAAAGAAAATGTGGAAAAGAGGGGCTGTGTAAT
GCATGTACTTGGAGACAAAACACTAAATCTTCAAGAATAGAAGCCATTAAG
ATACAAATCCTCAGTAAACTTCGTCTGGAAACAGCTCCTAACATCAGCAAA
GATGTTATAAGACAACTTTTACCCAAAGCTCCTCCACTCCGGGAACTGATT
GATCAGTATGATGTCCAGAGGGATGACAGCAGCGATGGCTCTTTGGAAGAT
GACGATTATCACGCTACAACGGAAACAATCATTACCATGCCTACAGAGTCT
GATTTTCTAATGCAAGTGGATGGAAAACCCAAATGTTGCTTCTTTAAATTT
AGCTCTAAATACAATACAATAAAGTAGTAAAGGCCCAACTATGGATATAT
TTGAGACCCGTCGAGACTCCTACAACAGTGTTTGTGCAAATCCTGAGACTC
ATCAAACCTATGAAAGACGGTACAAGGTATACTGGAATCCGATCTCTGAAA
CTTGACATGAACCCAGGCACTGGTATTTGGCAGAGCATTGATGTGAAGACA
GTGTTGCAAAATTGGCTCAAACAACCTGAATCCAACTTAGGCATTGAAATA
AAAGCTTTAGATGAGAATGGTCATGATCTTGCTGTAACCTTCCCAGGACCA
GGAGAAGATGGGCTGAATCCGTTTTTAGAGGTCAAGGTAACAGACACACCA
AAAAGATCCAGAAGG

Fig. 14G

SEQ ID NO:7 Human BMP-11 precursor protein - protein sequence

MVLAAPLLLGFLLLALELRPRGEAAEGPAAAAAAAAAAAAGVGGERSSRP
APSVAPEPDGCPVCVWRQHSRELRLESIKSQILSKLRLKEAPNISREVVKQ
LLPKAPPLQQILDLHDFQGDALQPEDFLEEDEYHATTETVISMAQETDPAV
QTDGSPLCCHFHFSPKVMFTKVLKAQLWVYLRPVPRPATVYLQILRLKPLT
GEGTAGGGGGGRRHIRIRSLKIELHSRSGHWQSIDFKQVLHSWFRQPQSNW
GIEINAFDPSGTDLAVTSLGPGAEGLHPFMELRVLENTKRSRRNLGLDCDE
HSSESRCCRYPLTVDFEAFGWDWIIAPKRYKANYCSGQCEYMFMQKYPHTH
LVQQANPRGSAGPCCTPTKMSPINMLYFNDKQQIIYGKIPGMVVDRCGCS

Fig. 14H

SEQ ID NO:8 Human BMP-11 precursor protein - DNA sequence

ATGGTGCTCGCGGCCCCGCTGCTGCTGGGCTTCCTGCTCCTCGCCCTGGA
GCTGCGGCCCCGGGGGGAGGCGGCCGAGGGCCCCGCGGCGGCGGCGGCGG
CGGCGGCGGCGGCAGCGGCGGGGGTCGGGGGGGAGCGCTCCAGCCGG
CCAGCCCCGTCCGTGGCGCCCGAGCCGGACGGCTGCCCCGTGTGCGTTTG
GCGGCAGCACAGCCGCGAGCTGCGCCTAGAGAGCATCAAGTCGCAGATCT
TGAGCAAACTGCGGCTCAAGGAGGCGCCCAACATCAGCCGCGAGGTGGTG
AAGCAGCTGCTGCCCAAGGCGCCGCCGCTGCAGCAGATCCTGGACCTACA
CGACTTCCAGGGCGACGCGCTGCAGCCCGAGGACTTCCTGGAGGAGGACG
AGTACCACGCCACCACCGAGACCGTCATTAGCATGGCCCAGGAGACGGAC
CCAGCAGTACAGACAGATGGCAGCCCTCTCTGCTGCCATTTTCACTTCAG
CCCCAAGGTGATGTTCACAAAGGTACTGAAGGCCCAGCTGTGGGTGTACC
TACGGCCTGTACCCCGCCCAGCCACAGTCTACCTGCAGATCTTGCGACTA
AAACCCCTAACTGGGGAAGGGACCGCAGGGGGAGGGGGCGGAGGCCGGCG
TCACATCCGTATCCGCTCACTGAAGATTGAGCTGCACTCACGCTCAGGCC
ATTGGCAGAGCATCGACTTCAAGCAAGTGCTACACAGCTGGTTCCGCCAG
CCACAGAGCAACTGGGGCATCGAGATCAACGCCTTTGATCCCAGTGGCAC
AGACCTGGCTGTCACCTCCCTGGGGCCGGGAGCCGAGGGGCTGCATCCAT
TCATGGAGCTTCGAGTCCTAGAGAACACAAAACGTTCCCGGCGGAACCTG
GGTCTGGACTGCGACGAGCACTCAAGCGAGTCCCGCTGCTGCCGATATCC
CCTCACAGTGGACTTTGAGGCTTTCGGCTGGGACTGGATCATCGCACCTA
AGCGCTACAAGGCCAACTACTGCTCCGGCCAGTGCGAGTACATGTTCATG
CAAAAATATCCGCATACCCATTTGGTGCAGCAGGCCAATCCAAGAGGCTC
TGCTGGGCCCTGTTGTACCCCCACCAAGATGTCCCCAATCAACATGCTCT
ACTTCAATGACAAGCAGCAGATTATCTACGGCAAGATCCCTGGCATGGTG
GTGGATCGCTGTGGCTGCTCT

Fig. 14I

SEQ ID NO:9 Human BMP-11 mature - protein sequence

NLGLDCDEHSSESRCCRYPLTVDFEAFGWDWIIAPKRYKANYCSGQCEYMF
MQKYPHTHLVQQANPRGSAGPCCTPTKMSPINMLYFNDKQQIIYGKIPGMV
VDRCGCS

Fig. 14J

SEQ ID NO:10 Human BMP-11 mature - DNA sequence

AACCTGGGTCTGGACTGCGACGAGCACTCAAGCGAGTCCCGCTGCTGCCG
ATATCCCCTCACAGTGGACTTTGAGGCTTTCGGCTGGGACTGGATCATCG
CACCTAAGCGCTACAAGGCCAACTACTGCTCCGGCCAGTGCGAGTACATG
TTCATGCAAAAATATCCGCATACCCATTTGGTGCAGCAGGCCAATCCAAG
AGGCTCTGCTGGGCCCTGTTGTACCCCCACCAAGATGTCCCCAATCAACA
TGCTCTACTTCAATGACAAGCAGCAGATTATCTACGGCAAGATCCCTGGC
ATGGTGGTGGATCGCTGTGGCTGCTCT

Fig. 14K

SEQ ID NO:11 Human BMP-11 propeptide - protein sequence

AEGPAAAAAAAAAAAAAGVGGERSSRPAPSVAPEPDGCPVCVWRQHSRELR
LESIKSQILSKLRLKEAPNISREVVKQLLPKAPPLQQILDLHDFQGDALQP
EDFLEEDEYHATTETVISMAQETDPAVQTDGSPLCCHFHFSPKVMFTKVLK
AQLWVYLRPVPRPATVYLQILRLKPLTGEGTAGGGGGRRHIRIRSLKIEL
HSRSGHWQSIDFKQVLHSWFRQPQSNWGIEINAFDPSGTDLAVTSLGPGAE
GLHPFMELRVLENTKRSRR

Fig. 14L

SEQ ID NO:12 Human BMP-11 propeptide - DNA sequence

GCCGAGGGCCCCGCGGCGGCGGCGGCGGCGGCGGCGGCGGCAGCGGC
GGGGGTCGGGGGGGAGCGCTCCAGCCGGCCAGCCCCGTCCGTGGCGCCCG
AGCCGGACGGCTGCCCCGTGTGCGTTTGGCGGCAGCACAGCCGCGAGCTG
CGCCTAGAGAGCATCAAGTCGCAGATCTTGAGCAAACTGCGGCTCAAGGA
GGCGCCCAACATCAGCCGCGAGGTGGTGAAGCAGCTGCTGCCCAAGGCGC
CGCCGCTGCAGCAGATCCTGGACCTACACGACTTCCAGGGCGACGCGCTG
CAGCCCGAGGACTTCCTGGAGGAGGACGAGTACCACGCCACCACCGAGAC
CGTCATTAGCATGGCCCAGGAGACGGACCCAGCAGTACAGACAGATGGCA
GCCCTCTCTGCTGCCATTTTCACTTCAGCCCCAAGGTGATGTTCACAAAG
GTACTGAAGGCCCAGCTGTGGGTGTACCTACGGCCTGTACCCCGCCCAGC
CACAGTCTACCTGCAGATCTTGCGACTAAAACCCCTAACTGGGGAAGGGA
CCGCAGGGGAGGGGCGGAGGCCGGCGTCACATCCGTATCCGCTCACTG
AAGATTGAGCTGCACTCACGCTCAGGCCATTGGCAGAGCATCGACTTCAA
GCAAGTGCTACACAGCTGGTTCCGCCAGCCACAGAGCAACTGGGGCATCG
AGATCAACGCCTTTGATCCCAGTGGCACAGACCTGGCTGTCACCTCCCTG
GGGCCGGGAGCCGAGGGGCTGCATCCATTCATGGAGCTTCGAGTCCTAGA
GAACACAAAACGTTCCCGGCGG

Fig. 14M

SEQ ID NO:13 GDF-8 signal sequence - protein sequence

MQKLQLCVYIYLFMLIVAGPVDL

Fig. 14N

SEQ ID NO:14 BMP-11 signal sequence - protein sequence

MVLAAPLLLGFLLLALELRPRGEA

Fig. 14O

SEQ ID NO:15 Human IgG1-Fc - protein sequence

EPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCL
VKGFYPSDIAVEWESNGQPENNYKTTPPVLDSDGSFFLYSKLTVDKSRWQQ
GNVFSCSVMHEALHNHYTQKSLSLSPGK

Fig. 14P

SEQ ID NO:16 Human IgG1-Fc modified - protein sequence

DKTHTCPPCPAPEALGAPSVFLFPPKPKDTLMISRTPEVTCVVVDVSHEDP
EVKFNWYVDGVEVHNAKTKPREEQYNSTYRVVSVLTVLHQDWLNGKEYKCK
VSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFS
CSVMHEALHNHYTQKSLSLSPGK

MODIFIED AND STABILIZED GDF PROPEPTIDES AND USES THEREOF

RELATED APPLICATIONS

This application claims the benefit of provisional application Ser. No. 60/267,509, filed on Feb. 8, 2001, the entire disclosure of which is hereby incorporated by reference.

FIELD OF THE INVENTION

This invention relates to inhibitors of Growth Differentiation Factor-8 (GDF-8) proteins and methods for their use. More particularly, the invention provides modified and stabilized propeptides of GDF-8 proteins which inhibit the activity of GDF-8. The invention is particularly useful for preventing or treating human or animal disorders in which an increase in skeletal muscle tissue would be therapeutically beneficial. Such disorders include muscle or neuromuscular disorders (such as amyotrophic lateral sclerosis, muscular dystrophy, muscle atrophy, congestive obstructive pulmonary disease, muscle wasting syndrome, sarcopenia, or cachexia), metabolic diseases or disorders (such as type 2 diabetes, noninsulin-dependent diabetes mellitus, hyperglycemia, or obesity), adipose tissue disorders (such as obesity), or bone degenerative diseases (such as osteoporosis).

BACKGROUND OF THE INVENTION

Growth and Differentiation Factor-8 (GDF-8), also known as myostatin, is a member of the Transforming Growth Factor-beta (TGF-β) superfamily of structurally related growth factors, all of which possess important growth-regulatory and morphogenetic properties (Kingsley et al. (1994) *Genes Dev.* 8:133–46; Hoodless et al. (1998) *Curr. Topics Microbiol. Immunol.* 228:235–72). GDF-8 is a negative regulator of skeletal muscle mass, and there is considerable interest in identifying factors which regulate its biological activity. For example, GDF-8 is highly expressed in the developing and adult skeletal muscle. The GDF-8 null mutation in transgenic mice is characterized by a marked hypertrophy and hyperplasia of the skeletal muscle (McPherron et al. (1997) *Nature* 387:83–90). Similar increases in skeletal muscle mass are evident in naturally occurring mutations of GDF-8 in cattle (Ashmore et al. (1974) *Growth* 38:501–507; Swatland and Kieffer (1994) *J. Anim. Sci.* 38:752–757; McPherron and Lee (1997) *Proc. Natl. Acad. Sci. U.S.A.* 94:12457–12461; and Kambadur et al. (1997) *Genome Res.* 7:910–915). Recent studies have also shown that muscle wasting associated with HIV-infection in humans is accompanied by increases in GDF-8 protein expression (Gonzalez-Cadavid et al. (1998) *PNAS* 95:14938–43). In addition, GDF-8 can modulate the production of muscle-specific enzymes (e.g., creatine kinase) and modulate myoblast cell proliferation (WO 00/43781).

In addition to its growth-regulatory and morphogenetic properties in skeletal muscle, GDF-8 may also be involved in a number of other physiological processes (e.g., glucose homeostasis), as well as abnormal conditions, such as in the development of type 2 diabetes and adipose tissue disorders, such as obesity. For example, GDF-8 modulates preadipocyte differentiation to adipocytes (Kim et al. (2001) *B.B.R.C.* 281:902–906).

Like TGF-β-1, -2, and -3, the GDF-8 protein is synthesized as a precursor protein consisting of an amino-terminal propeptide and a carboxy-terminal mature domain (McPherron and Lee, 1997, supra) as well as a signal sequence which directs the protein to the extracellular domain and is also cleaved from the protein. It is believed that before cleavage of the propeptide, the precursor GDF-8 protein forms a homodimer. The amino-terminal propeptide is then cleaved from the mature domain and the cleaved propeptide may remain noncovalently bound to the mature domain dimer, inhibiting its biological activity (Miyazono et al. (1988) *J. Biol. Chem.* 263:6407–6415; Wakefield et al. (1988) *J. Biol. Chem.* 263:7646–7654; and Brown et al. (1990) *Growth Factors* 3:35–43). It is believed that two GDF-8 propeptides bind to the GDF-8 mature dimer (Thies et al. (2001) *Growth Factors* 18:251–259). Due to this inactivating property, the propeptide is known as the "latency-associated peptide" (LAP), and the complex of mature domain and propeptide is commonly referred to as the "small latent complex" (Gentry and Nash (1990) *Biochemistry* 29:6851–6857; Derynck et al. (1995) *Nature* 316:701–705; and Massague (1990) *Ann. Rev. Cell Biol.* 12:597–641). The mature domain is believed to be active as a homodimer when the propeptide is removed. Other proteins are also known to bind to GDF-8 or structurally related proteins and inhibit their biological activity. Such inhibitory proteins include follistatin (Gamer et al. (1999) *Dev. Biol.* 208:222–232) and follistatin-related proteins.

Further, a number of human and animal disorders are associated with loss of or functionally impaired muscle tissue, including muscular dystrophy, muscle atrophy, congestive obstructive pulmonary disease, muscle wasting syndrome, sarcopenia, and cachexia. To date, very few reliable or effective therapies exist for these disorders. The terrible symptoms associated with these disorders could be substantially reduced by employing therapies that increase the amount of muscle tissue in patients suffering from the disorders. Such therapies would significantly improve the quality of life for these patients and could ameliorate many effects of these diseases. Thus, there is a need in the art to identify new therapies that contribute to an overall increase in muscle tissue in patients suffering from these disorders.

The present invention fills this need by providing modified and stabilized GDF propeptides that retain their biological activity and inhibit the activity of GDF proteins. The modified propeptides of the invention may be used to treat human or animal disorders in which an increase in muscle tissue would be therapeutically beneficial.

SUMMARY OF THE INVENTION

GDF-8 is involved in the regulation of many critical biological processes. Due to its key function in these processes, GDF-8 may be a desirable target for therapeutic intervention. Although naturally occurring GDF-8 propeptide may be an attractive means of GDF modulation from an efficacy and toxicity perspective, the present inventors have discovered that the circulatory half-life of the natural propeptide may be too short for the molecule to have practical therapeutic or prophylactic utility.

Accordingly, the present invention is based, at least in part, on the discovery that the propeptide of Growth Differentiation Factor-8 (GDF-8) inhibits the activity of GDF-8 protein, and that other Transforming Growth Factor-beta (TGF-β) proteins which are related in structure to GDF-8, such as Bone Morphogenetic Protein-11 (BMP-11; also known as GDF-11), are also inhibited by GDF-8 propeptide. The present invention thus provides compositions and methods for inhibiting GDF proteins, as well as methods for identifying, making and using such inhibitors.

As noted above, the present invention is also based, in part, on the discovery that the natural GDF-8 propeptide has a relatively short in vivo half-life, which may prevent practical therapeutic or prophylactic utility. Thus, the present invention provides modified GDF-8 propeptides and modified BMP-11 propeptides having improved pharmacokinetic properties, such as increased circulatory half-life or increased protection from proteolytic degradation.

The presently disclosed GDF-8 propeptides or BMP-11 propeptides may be stabilized by any means known in the art. For example, in one embodiment, the modified propeptide is a fusion protein comprising a GDF-8 propeptide and the Fc region of an IgG molecule. GDF-8 propeptide fusion proteins may comprise, as the active subunit, the propeptide of a GDF-8 protein, or an active portion of the GDF-8 propeptide, fused to an Fc region of an IgG molecule. In other embodiments, or in addition, the GDF-8 propeptide may be glycosylated, or linked to albumin or a nonproteineous polymer.

In other embodiments, the modified propeptide is a fusion protein comprising a BMP-11 propeptide and the Fc region of an IgG molecule. BMP-11 propeptide fusion proteins may comprise, as the active subunit, the propeptide of a BMP-11 protein, or an active portion of the BMP-11 propeptide, fused to an Fc region of an IgG molecule. In other embodiments, or in addition, the BMP-11 propeptide may be glycosylated, or linked to albumin or a nonproteineous polymer.

The modified GDF-8 propeptides or modified BMP-11 propeptides of the invention are capable of inhibiting the activity, expression, processing, or secretion of a GDF-8 protein, mature GDF-8, or a GDF-8 homodimer or other active GDF-8 molecule. The modified GDF-8 propeptides or modified BMP-11 propeptides of the invention may be administered to a patient, in a therapeutically effective dose, to treat or prevent medical conditions in which an increase in muscle tissue would be therapeutically beneficial. Diseases and disorders that may be treated by the modified GDF-8 propeptides or modified BMP-11 propeptides include but are not limited to muscle or neuromuscular disorders (such as amyotrophic lateral sclerosis, muscular dystrophy, muscle atrophy, congestive obstructive pulmonary disease, muscle wasting syndrome, sarcopenia, or cachexia), metabolic diseases or disorders (such as such as type 2 diabetes, noninsulin-dependent diabetes mellitus, hyperglycemia, or obesity), adipose tissue disorders (such as obesity), and bone degenerative diseases (such as osteoporosis).

BRIEF DESCRIPTION OF THE FIGURES

FIG. 7A shows the amino acid sequence of a murine GDF-8 propeptide-Fc fusion protein, as provided in SEQ ID NO:20.

FIG. 7B shows a murine GDF-8 propeptide-Fc fusion protein with a short glycine-serine-glycine-serine (GSGS, SEQ ID NO:17) linker separating the GDF-8 propeptide from the Fc region, as provided in SEQ ID NO:21.

FIG. 11A shows the amino acid sequence of a human GDF-8 propeptide IgG1 Fc fusion protein, as provided in SEQ ID NO:22.

FIG. 11B shows the amino acid sequence of a human GDF-8 propeptide-IgG1 Fc fusion protein modified for reduced effector function, as provided in SEQ ID NO:23.

FIGS. 14A–P illustrate the amino acid and nucleic acid sequences corresponding to SEQ ID NO.s 1–16 and annotations thereto.

DEFINITIONS

Figure 1:
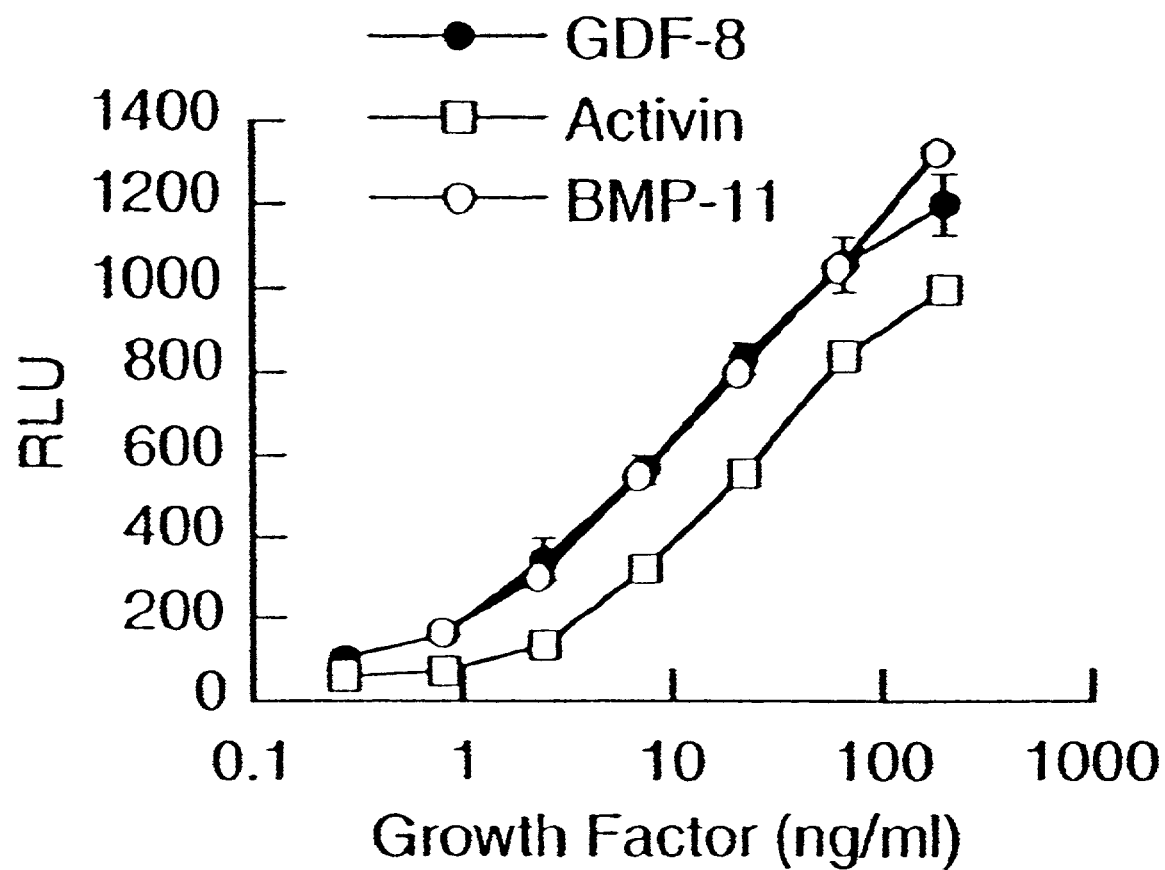
FIG. 1 shows the relative biological activities of GDF-8, BMP-11 and activin in a reporter gene assay.

The terms "GDF-8", "GDF-8 protein", or "GDF-8 polypeptide" refer to a specific growth and differentiation factor including but not limited to that set forth in SEQ ID NO: 1, and any now known or later described homologs thereof, including homologs of other species. Particularly preferred are mammalian homologs, most preferably human. The present invention also encompasses GDF-8 molecules and homologs from all other sources, including but not limited to GDF-8 from bovine, dog, cat, chicken, murine, rat, porcine, ovine, turkey, baboon, and fish. Various GDF-8 molecules have been described in McPherron et al. (1997) *Proc. Natl. Acad. Sci. USA* 94:12457–12461. Homologs are well known in the art. Homology may be determined by any method known in the art, or as described herein. The GDF-8 or GDF-8 protein may be naturally occurring or synthetic. These terms include the full-length unprocessed precursor form of the protein ("GDF-8 precursor protein"), as well as the mature forms resulting from post-translational cleavage of the propeptide. The terms also refer to any fragments or variants of GDF-8 that maintain one or more biological activities associated with a GDF-8 protein, as discussed herein, including sequences that have been modified with conservative or non-conservative changes to the amino acid sequence.

"Mature GDF-8" refers to the protein or polypeptide that is cleaved from the carboxy-terminal domain of the GDF-8 precursor protein. A human form of mature GDF-8 protein is provided in SEQ ID NO:3. The mature GDF-8 may be naturally occurring or synthetic. The mature GDF-8 may be present as a monomer, homodimer, or may be present in a GDF-8 latent complex. Depending on the in vivo or in vitro conditions, mature GDF-8 may establish an equilibrium among any or all of these different forms. Without limitation as to the mechanism, mature GDF-8 is believed to be biologically active as homodimer. In its biologically active form, the mature GDF-8 is also referred to as "active GDF-8."

The phrase "GDF-8 activity" refers to one or more of physiologically growth-regulatory or morphogenetic activities associated with active GDF-8 protein. For example, active GDF-8 is a negative regulator of skeletal muscle mass. Active GDF-8 can also modulate the production of muscle-specific enzymes (e.g., creatine kinase), stimulate myoblast cell proliferation, and modulate preadipocyte differentiation to adipocytes. GDF-8 also believed to increase sensitivity to insulin and glucose uptake in peripherial tissues, particularly in skeletal muscle or adipocytes. Accordingly, GDF-8 biological activities include but are not limited to inhibition of muscle formation, inhibition of muscle cell growth, inhibition of muscle development, decrease in muscle mass, regulation of muscle-specific enzymes, inhibition of myoblast cell proliferation, modulation of preadipocyte differentiation to adipocytes, increasing sensitivity to insulin, regulations of glucose uptake, glucose hemostasis, and modulate neuronal cell development and maintenance. A human form of the full length GDF-8 precursor protein is provided in SEQ ID NO: 1.

"GDF-8 propeptide" refers to a polypeptide that is cleaved from the amino-terminal domain of the GDF-8 precursor protein. The GDF-8 propeptide is associated with one or more biological activities including but not limited to the ability to bind to a mature GDF-8 protein or homodimer, the ability to inhibit one or more GDF-8 biological activities, the ability to enhance muscle development, the ability to enhance muscle mass, the ability to promote muscle formation, and the ability to promote muscle cell proliferation. The GDF-8 propeptide may be naturally occurring or synthetic. An example of a GDF-8 propeptide includes but is not limited to a human form of GDF-8 propeptide provided in SEQ ID NO: 5. In one embodiment, the GDF-8 propeptide is capable of binding to the propeptide binding domain of mature GDF-8. In another embodiment, the GDF-8 propeptide is capable of inhibiting one or more activities of a mature GDF-8.

The term "GDF-8 inhibitor" includes any agent capable of inhibiting the activity, expression, processing, or secretion of a GDF-8 protein, mature GDF-8, or a GDF-8 homodimer or other active GDF-8 molecule including but not limited to modified GDF-8 propeptides and modified BMP-11 propeptides. A GDF-8 inhibitor also includes any agent capable of enhancing the binding of a GDF-8 propeptide to a mature GDF-8 molecule, or to a GDF-8 homodimer. Such inhibitors include but are not limited to proteins, antibodies, peptides, peptidomimetics, ribozymes, anti-sense oligonucleotides, double-stranded RNA, and other small molecules. In one embodiment, the activity of a GDF-8 protein is inhibited by a modified GDF-8 propeptide as described in Examples 3–6. In another embodiment, the activity of a GDF-8 protein is inhibited by a modified BMP-11 propeptide.

"GDF-8 latent complex" refers to a complex of proteins formed between a mature GDF-8 homodimer and a GDF-8 propeptide. Without limitation as to mechanism it is believed that two GDF-8 propeptides associate with two molecules of mature GDF-8 in the homodimer to form an inactive tetrameric or latent complex. The latent complex may include other GDF inhibitors in place of or in addition to one or more of the GDF-8 propeptides.

The term "modified GDF-8 propeptide" refers to a GDF-8 inhibitor which comprises a modified GDF-8 propeptide, fragment or variant thereof which retains one or more biological activities of a GDF-8 propeptide and further comprises a stabilizing modification as set forth herein. Variant forms of GDF-8 propeptide, include, but are not limited to, for example, GDF-8 propeptides that have been modified to include mutations (including insertion, deletion, and substitution of amino acids) in the signal peptide or propeptide proteolytic cleavage sites to make the sites less susceptible to proteolytic cleavage. In a preferred embodiment, the modified GDF-8 propeptide has a substantially increased half life relative to that of the corresponding unmodified GDF-8 propeptide. In a highly preferred embodiment, the modified GDF-8 propeptide of the invention has an increased in vivo half life (as measured, for example, by the method set forth in Example 8). In another embodiment, the modified GDF-8 propeptide is capable of inhibiting one or more activities of a mature GDF-8.

The terms "BMP-11", "BMP-11 protein", or "BMP-11 polypeptide" refer to a specific growth and differentiation factor including but not limited to that set forth in SEQ ID NO:7, and any now known or later described homologs thereof, including homologs of other species. Particularly preferred are mammalian homologs, most preferably human. The present invention also encompasses BMP-11 molecules and homologs from all other sources, including but not limited to BMP-11 from bovine, dog, cat, chicken, murine, rat, porcine, ovine, turkey, baboon, and fish. Various BMP-11 molecules have been described in McPherron et al. (1997) *Proc. Natl. Acad. Sci. USA* 94:12457–12461. Homologs are well known in the art. Homology may be determined by any method known in the art, or as described herein. The BMP-11 or BMP-11 protein may be naturally occurring or synthetic. These terms include the full-length unprocessed precursor form of the protein ("BMP-11 precursor protein"), as well as the mature forms resulting from post-translational cleavage of the propeptide. The terms also refer to any fragments or variants of BMP-11 that maintain one or more biological activities associated with a BMP-11 protein, as discussed herein, including sequences that have been modified with conservative or non-conservative changes to the amino acid sequence.

"Mature BMP-11" refers to the protein or polypeptide that is cleaved from the carboxy-terminal domain of the BMP-11 precursor protein. A human form of mature BMP-11 protein is provided in SEQ ID NO:9. The mature BMP-11 may be naturally occurring or synthetic. The mature BMP-11 may be present as a monomer, homodimer, or may be present in a BMP-11 latent complex. Depending on the in vivo or in vitro conditions, mature BMP-11 may establish an equilibrium among any or all of these different forms. Without limitation as to the mechanism, mature BMP-11 is believed to be biologically active as homodimer. In its biologically active form, the mature BMP-11 is also referred to as "active BMP-11."

"BMP-11 propeptide" refers to a polypeptide that is cleaved from the amino-terminal domain of the BMP-11 precursor protein. The BMP-11 propeptide is associated with one or more biological activities including but not limited to the ability to bind to a mature GDF-8 protein or homodimer, the ability to inhibit one or more GDF-8 biological activities, the ability to enhance muscle development, the ability to enhance muscle mass, the ability to promote muscle formation, and the ability to promote muscle cell proliferation. The BMP-11 propeptide may be naturally occurring or synthetic. An example of a BMP-11 propeptide includes but is not limited to a human form of BMP-11 provided in SEQ ID NO:11. In one embodiment, the BMP-11 propeptide is capable of binding to the propeptide binding domain of mature GDF-8. In another embodiment, the BMP-11 propeptide is capable of inhibiting one or more activities of a mature GDF-8.

The term "modified BMP-11 propeptide" refers to a GDF-8 inhibitor which comprises a modified BMP-11 propeptide, or fragment or variant thereof, which retains one or more biological activities of a BMP-11 propeptide and further comprises a stabilizing modification as set forth herein. Variant forms of BMP-11 propeptide, include, but are not limited to, for example, BMP-11 propeptides that have been modified to include mutations (including insertion, deletion, and substitution of amino acids) in the signal peptide or propeptide proteolytic cleavage sites to make the sites more or less susceptible to proteolytic cleavage. In a preferred embodiment, the BMP-11 propeptide inhibitor is modified to provide an increased in vivo half life (measured in one embodiment in Example 8) relative to that of the corresponding unmodified BMP-11 propeptide. In another embodiment, the modified BMP-11 propeptide is capable of inhibiting one or more activities of a mature GDF-8.

The GDF-8 propeptides of the invention and BMP-11 propeptides of the invention are collectively referred to as "GDF propeptides."

The GDF-8 proteins of the invention and the BMP-11 proteins of the invention are collectively referred to as "GDF polypeptides" or "GDF proteins."

The methods and compositions of the invention provide GDF inhibitors which reduce the activity of GDF protein relative to the activity of a GDF protein as compared to the same GDF protein not bound by an inhibitor. In certain embodiments, the activity of a GDF protein, when bound by one or more of the modified GDF propeptides is reduced at least about 10%, 15%, 20%, 25%, 30%, 35%, 40%, 45%, 50%, or 55%, preferably at least about 60%, 62%, 64%, 66%, 68%, 70%, 72%, 74%, 76%, 78%, 80%, 82%, 84%, 86%, or 88%, more preferably at least about 90%, 91%, 92%, 93%, or 94%, and even more preferably at least about 95% to 100% relative to the same GDF protein that is not bound by said modified propeptides. In one preferred embodiment, the GDF inhibitor is a modified GDF-8 propeptide or a modified BMP-11 propeptide covalently linked to an Fc region of an IgG molecule.

The term "stabilizing modification" is any modification known in the art or set forth herein capable of stabilizing a protein, enhancing the in vitro half life of a protein, enhancing circulatory half life of a protein and/or reducing proteolytic degradation of a protein. Such stabilizing modifications include but are not limited to fusion proteins (including, for example, fusion proteins comprising a GDF propeptide and a second protein), modification of a glycosylation site (including, for example, addition of a glycosylation site to a GDF propeptide), and modification of carbohydrate moiety (including, for example, removal of carbohydrate moieties from a GDF propeptide). In the case of a stabilizing modification which comprises a fusion protein (e.g., such that a second protein is fused to a GDF propeptide), the second protein may be referred to as a "stabilizer portion" or "stabilzer protein." For example, in one embodiment, a modified GDF-8 propeptide of the invention comprises a fusion between a human GDF-8 propeptide (with an inactivated cleavage site) and an IgG molecule (which IgG acts as the stabilizer protein or stabilizer portion). As used herein, in addition to referring to a second protein of a fusion protein, a "stabilizer portion" also includes nonproteinaceous modifications such as a carbohydrate moiety, or nonproteinaceous polymer.

The terms "isolated" or "purified" refer to a molecule that is substantially free of its natural environment. For instance, an isolated protein is substantially free of cellular material or other contaminating proteins from the cell or tissue source from which it is derived. The phrase "substantially free of cellular material" refers to preparations where the isolated protein is at least 70% to 80% (w/w) pure, more preferably at least 80–89% (w/w) pure, even more preferably 90–95% pure, and most preferably at least 96%, 97%, 98%, 99% or 100% (w/w) pure.

The term "cleavage site" refers to a proteolytic site in a protein or polypeptide that is acted upon by a proteolytic enzyme resulting in the cleavage of the peptide bond. In one embodiment, a cleavage site of the invention is "RSRR" as represented by the one-letter amino acid code.

The term "Fc region of an IgG molecule" refers to the Fc domain of an immunoglobulin of the isotype IgG, as is well known to those skilled in the art. The Fc region of an IgG molecule is that portion of IgG molecule (IgG1, IgG2, IgG3, and IgG4) that is responsible for increasing the in vivo serum half-life of the IgG molecule. Preferably, the IgG molecule is IgG1.

"In vitro half life" refers to the stability of a protein measured outside the context of a living organism. Assays to measure in vitro half life are well known in the art and include but are not limited to SDS-PAGE, ELISA, cell-based assays, pulse-chase, western blotting, northern blotting, etc. There and other useful assays are well known in the art.

"In vivo half life" refers to the stability of a protein in an organism. In vivo half life may be measured by a number of methods known in the art including but not limited to in vivo serum half life, circulatory half life, and assays set forth in the examples herein.

"In vivo serum half life" refers to the half-life of a protein circulating in the blood of an organism. In one embodiment, in vivo half life is measured as set forth in Example 8. Other methods known in the art may be used to measure in vivo half life.

The term "mammal" includes definitions known in the art and also refers to any animal classified as a mammal, including humans, domestic and farm animals, and zoo, sports, or pet animals, such as dogs, cats, sheep, pigs, cows, etc. In a preferred embodiment, the mammal is human.

The term "TGF-β superfamily" refers to a family of structurally related growth factors, all of which possess physiologically important growth-regulatory and morphogenetic properties. This family of related growth factors is well known in the art (Kingsley et al. (1994) *Genes Dev.* 8:133–46; and Hoodless et al. (1998) *Curr. Topics Microbiol. Immunol.* 228:235–72). The TGF-β superfamily includes Bone Morphogenetic Proteins (BMPs), Activins, Inhibins, Mullerian Inhibiting Substance, Glial-Derived Neurotrophic Factor, and a still growing number of Growth and Differentiation Factors (GDFs), such as GDF-8 (myostatin). Many of these proteins are related in structure to GDF-8, such as BMP-11 (also known as GDF-11), and/or activity, such as activin.

The term "treatment" refers to both therapeutic treatment and prophylactic or preventative measures. Those in need of treatment may include individuals already having a particular medical disorder as well as those who may ultimately acquire the disorder (i.e., those needing preventative measures).

The terms "transformation" and "transfection" refer to a variety of art-recognized techniques for introducing foreign nucleic acid (e.g., DNA and RNA) into a host cell, including but not limited to calcium phosphate or calcium chloride co-precipitation, DEAE-dextran-mediated transfection, lipofection, and electroporation.

| SEQ ID NO: | NAME | TYPE |
|---|---|---|
| 1 | human GDF-8 precursor protein | protein |
| 2 | human GDF-8 precursor protein | DNA |
| 3 | human GDF-8 mature | protein |
| 4 | human GDF-8 mature | DNA |
| 5 | human GDF-8 propeptide | protein |
| 6 | human GDF-8 propeptide | DNA |
| 7 | human BMP-11 precursor protein | protein |
| 8 | human BMP-11 precursor protein | DNA |
| 9 | human BMP-11 mature | protein |
| 10 | human BMP-11 mature | DNA |
| 11 | human BMP-11 propeptide | protein |
| 12 | human BMP-11 propeptide | DNA |
| 13 | GDF-8 signal sequence | protein |
| 14 | BMP-11 signal sequence | protein |
| 15 | IgG-Fc | protein |
| 16 | IgG-Fc modified | protein |

DETAILED DESCRIPTION OF THE INVENTION

The present invention is based, in part, on the discovery that GDF propeptides have a short in vivo half-life thereby reducing their effectiveness as pharmocologic inhibitors of GDF-8 or BMP-11 activity. Accordingly, in one aspect, the invention features modified and stabilized GDF-8 or BMP-11 propeptide having improved pharmacokinetic properties, specifically an increased circulatory half-life.

The present invention provides novel modified GDF propeptides that form inactive complexes with GDF proteins (for example GDF-8 and BMP-11 proteins) in vitro and in vivo. The modified GDF propeptides of the invention preferably bind to a propeptide binding domain on the mature GDF protein. Accordingly, in certain embodiments of the invention, the modified GDF propeptide comprises a fusion protein between a GDF propeptide and a stabilizer protein. A stabilizer protein may be any protein which enhances the overall stability of the modified GDF propeptide. As will be recognized by one of ordinary skill in the art, such fusion protein may optionally comprise a linker peptide between the propeptide portion and the stabilizing portion. As is well known in the art, fusion proteins are prepared such that the second protein is fused in frame with the first protein such that the resulting translated protein comprises both the first and second proteins. For example, in the present invention, a fusion protein may be prepared such that the GDF propeptide portion is fused to a second protein (e.g. a stabilizer protein portion.) Such fusion protein is prepared such that the resulting translated protein contains both the propeptide portion and the stabilizer portion.

In other embodiments, the GDF propeptide comprises a GDF propeptide that is modified to have greater in vivo circulatory half-life compared to unmodified GDF propeptide. Although the precise mechanism and timing of modified GDF propeptide binding is unknown, the modified GDF-8 propeptides and modified BMP-11 propeptides of the invention are believed to bind to the mature GDF-8 and mature BMP-11. In a preferred embodiment, the present invention provides modified GDF propeptides that form inactive complexes with GDF-8 or BMP-11 proteins in vivo or in vitro. In one embodiment, the GDF propeptides preferably bind to a propeptide binding domain on the mature GDF-8 or mature BMP-11 protein. Such binding may occur, for example, following release of native propeptide at the site of GDF-8 and BMP-11 activity, following displacement of the native propeptide by the modified GDF-8 and modified BMP-11 propeptide, and/or following cleavage of propeptide from the GDF-8 and BMP-11 precursor protein. Regardless of the mechanism, modified GDF-8 propeptide and/or modified BMP-11 propeptide binding results in a reduction in one or more of the biological activities associated with GDF-8, relative to a mature GDF-8 protein that is not bound by the same modified propeptide. In one preferred embodiment, the modified GDF-8 and BMP-11 propeptides reduce GDF-8 and BMP-11 activity associated with negative regulation of skeletal muscle mass.

In another preferred embodiment, the present invention provides modified GDF propeptides that form inactive complexes with BMP-11 proteins in vivo or in vitro. In one embodiment, the GDF propeptides preferably bind to a propeptide binding domain on the mature BMP-11 protein. In yet another embodiment, the modified GDF propeptide is a fusion protein comprising a GDF propeptide and an Fc region of an IgG molecule (as a stabilizing protein). Such GDF inhibitors may comprise a GDF propeptide (for example as set forth in SEQ ID NO: 5 or 11) or a fragment or variant of said propeptide which retains one or more biological activities of a GDF propeptide. Such modified GDF propeptides are capable of inhibiting the activity of GDF proteins. The GDF-8 or BMP-11 propeptides used in the invention may be synthetically produced, derived from naturally occurring (native) GDF-8 or BMP-11 propeptides, or be produced recombinantly, using any of a variety of reagents, host cells and methods which are well known in the art of genetic engineering. In one embodiment, the modified GDF-8 propeptide or modified BMP-11 propeptide comprises a human GDF-8 or BMP-11 propeptide covalently linked to an IgG molecule or a fragment thereof. The GDF-8 or BMP-11 propeptide may be fused adjacent to the Fc region of the IgG molecule, or attached to the Fc region of the IgG molecule via a linker peptide. Use of such linker peptides is well known in the protein biochemistry art.

In certain embodiments where the modified GDF propeptides of the invention comprise fusion proteins, the GDF propeptide portion of said fusion protein is preferably at least about 75–80% identical to SEQ ID NO: 5 or 11, more preferably at least about 81% to about 85% identical to SEQ ID NO: 5 or 11, even more preferably at least about 86%, 87%, 88%, 89%, 90%, 91%, 92%, 93%, or 94% identical to SEQ ID NO: 5 or 11, and even more preferably at least about 95%, 96%, 97%, 98%, 99%, or 100% identical to SEQ ID NO: 5 or 11. In a preferred embodiment, the GDF-8 or BMP-11 propeptides comprise a sequence identical to the sequences set forth in SEQ ID NO: 5 or 11. In yet another preferred embodiment, the GDF propeptide portion of a fusion protein of the invention may comprise a fragment of variant of the GDF propeptide set forth in SEQ ID NO: 5 or 11, so long as the fragment or variant retains one or more biological activities of a GDF propeptide. In another preferred embodiment, the modified GDF-8 or BMP11 propeptides comprise a mutant version of SEQ ID NO: 5 or 11, wherein the mutant has been modified to include one or more mutations (including insertion, deletion, or substitution) so long as the fragment or variant retains one or more biological activities of a GDF propeptide.

Critically, in embodiments of the invention involving modified GDF propeptides comprising fusion proteins, it is essential that the fusion protein be produced or designed such that the native proteolytic cleavage site (e.g. RSRR (SEQ ID NO:18)) in the GDF propeptide is disrupted, destroyed, inactivated or removed in the resulting fusion protein. As one of skill in the art will recognize, failure to do so would result in the second protein (e.g., the stabilizer portion) of the fusion protein being cleaved from the first protein (the propeptide portion) of the fusion protein. Accordingly, a critical aspect of the invention provides for inactivating or eliminating the cleavage site native to GDF propeptides when using such propeptide to prepare a fusion protein which is a modified GDF propeptide of the invention. Methods for inactivating such proteolytic cleavage sites are known in the art and include but are not limited to mutation, deletion, or insertion of the amino acid or nucleotide sequence of the proteolytic cleavage site.

In yet other embodiments of the invention, mutations may be made in the GDF sequence to make the sites less susceptible to proteolytic cleavage. For example, in one embodiment, such mutant may contain a point mutation at amino acids 45, 46, 49, 50, 52, 53, 63, 64, 65, 66, 98 or 99 of SEQ ID NO: 1, or at amino acids 122, 123, 286 or 287 of SEQ ID NO: 7. In another embodiment, such point mutations can be made in the amino acids of SEQ ID NO.:11. In a preferred embodiment, the point mutation is a point mutation at amino acid 99 of SEQ ID NO:1. In a particularly preferred embodiment, the point mutation is a point mutation of amino acid 99 of SEQ ID NO.:1 from Asp to Ala. In another preferred embodiment, such point mutation can be made in the amino acids of SEQ ID NO.:11. Computer analysis (using a commercially available software, e.g., MacVector, Omega, PCGene, Molecular Simulation, Inc.) can also be used to identify proteolytic cleavage sites. As will be recognized by one of skill in the art any of the described mutations, variants or modifications may alternatively be made at the nucleic acid level. Such techniques are well known in the art.

TABLE 2

Exemplary Amino Acids Mutatable to Prevent Cleavage of Propeptide:

GDF-8 (Amino acid numbers refer to SEQ ID NO:1)

Arg-45

Gln-46

Lys-49

Ser-50

Arg-52

Ile-53

Lys-63

Leu-64

Arg-65

Leu-66

Arg-98

Asp-99

TABLE 2-continued

Exemplary Amino Acids Mutatable to Prevent Cleavage of Propeptide:

BMP-11 (Amino acids numbers refer to SEQ ID NO:7)

Asp-122

Ala-123

Glu-286

Leu-287

As noted above, the present inventors have made the discovery that the GDF propeptides have a short in vivo half-life. Thus, to be pharmaceutically useful as a therapeutic or prophylactic agent, the GDF propeptide must be chemically or physically stabilized for increased longevity under physiological conditions.

GDF propeptides may be stabilized or modified by any means known in the art, so long as the modified GDF propeptide maintains an ability to inhibit a GDF protein or mature GDF protein. In a preferred embodiment, the modified GDF propeptide maintains its ability to bind to its target GDF protein or a GDF propeptide binding site. In one preferred embodiment, the modified GDF propeptide comprises a GDF-8 propeptide or BMP-11 propeptide fused adjacent to or via a linker, to an Fc region of an IgG molecule. The Fc region of the IgG provides a protective or stabilizing effect on the propeptide (and therby acts as a stabilizing modification), as reflected in the improved pharmacokinetic properties (i.e., increased serum half-life) of the fusion protein as compared to the corresponding unmodified GDF-8 propeptide or unmodified BMP-11 propeptide.

In a particular embodiment, the modified GDF-8 propeptide comprises a human GDF-8 propeptide or a mutant of human GDF-8 propeptide, and the IgG molecule is the Fc region of an IgG1, or an IgG4, or an Fc region of IgG1 modified for reduced effector function. In one embodiment, the IgG fragment is IgG1 (SEQ ID NO: 15). In another embodiment, the IgG fragment is IgG1 modified for reduced effector function (SEQ ID NO:16). Examples of molecules modified for reduced effector function include modification of human IgG1-Fc fusion to include alanine (A) at amino acid positions 14 and 17 as set forth in SEQ ID NO.:16.

Modified GDP-8 or BMP-11 propeptides may be isolated or purified according to standard protein isolation and purification procedures well known in the art.

In another embodiment, the modified GDF propeptide comprises a human BMP-11 propeptide or a mutant of human BMP-11 propeptide, and an IgG molecule which is the Fc region of an IgG1, or an IgG4, or an IgG1 fragment modified for reduced effector function. In one preferred embodiment, the stabilizer is the Fc region of human IgG1 (SEQ ID NO: 15) or the Fc region of human IgG1 modified for reduced effector function (SEQ ID NO: 16). The BMP-11 propeptide may be fused adjacent to or via a linker, to an Fc region of an IgG molecule, as described herein.

The present invention also provides methods for making modified GDF propeptides having increased in vivo or in vitro half-life. In one preferred embodiment, the method comprises preparing a modified GDF propeptide comprising a GDF-8/IgG1 Fc or BMP-11 IgG1 Fc fusion protein by preparing a cDNA molecule encoding:

(1) a GDF propeptide (for example human GDF-8 propeptide, SEQ ID NO:5), or human BMP-11 propeptide, SEQ ID NO:11) which is modified to inactivate the proteolytic cleavage site and the Fc region of an IgG molecule (for example, human IgG1 Fc region, SEQ ID NO:15);

(2) expressing the cDNA in an appropriate prokaryotic or eukaryotic expression system using appropriate expression plasmids and cells; and (3) isolating and purifying the expressed fusion protein containing the modified GDF propeptide, wherein the modified GDF propeptide has an increased in vivo or in vitro half-life as compared to an unmodified GDF propeptide.

An example of such preferred modified GDF propeptide of the invention is set forth is FIG. 11A.

cDNA expression systems are well known in the molecular biology art as are methods for isolation and purification of the expressed proteins (Examples 2 and 7, herein, provide examples of such embodiments).

In an alternate embodiment, the cDNA constructs used for expression of such fusion proteins may contain nucleotides encoding a linker peptide between the nucleotides encoding the GDF propeptide and the IgG Fc region (or stabilizer portion). The orientation of the linker peptide relative to the GDF or IgG Ec region is unimportant. The linker peptide may comprise nucleotides encoding 2, 4, 6, 8, 10, 12, 14, 16, 18, 20, 22, 24, 26, 28, 30 or more amino acids in length. In a particular embodiment, the linker peptide comprises nucleotides encoding for the amino acid sequence consisting of glycine-serine-glycine-serine (GSGS. SEQ ID NO:17).

In another embodiment, the expression plasmids may optionally contain tags allowing for convenient isolation and purification of the expressed proteins. The use of such tagged expression plasmids and the methods for isolating and purifying the tagged protein products are well known in the art.

The GDF propeptides of the invention specifically include fusion proteins in which the GDF propeptide portion of the molecule is identical or greater than 60% homologous to GDF corresponding sequences from a particular species, while the stabilizer portion, such as the Fc region of the IgG molecule may be identical or greater than 60% homologous to IgG corresponding sequences from a different species. For example, the human GDF-8 propeptide or fragment thereof may be fused to an Fc region of a mouse IgG molecule, or vice versa, so long as the resulting fusion protein exhibits the desired biological activity, namely, the inhibition of GDF biological activity, as embodied in Examples 3–6. In preferred embodiments of the invention, fusion proteins of the invention are chimeras of human proteins. As will be understood in the art, human protein chimeric or fusion proteins will be preferred in the treatment of human subjects.

As an alternative or in addition to the above-described Fc-fusion proteins, the GDF propeptides may be stabilized by a variety of other methods and resource materials which are well known and readily available in the protein art. Such methods and materials include, for example, glycosylation, or linkage to albumin or a nonproteineous polymer, as described in detail below. The modified GDF propeptides may be isolated and purified using standard protein isolation and purification techniques well known in the protein art.

GDF propeptides or modified GDF propeptides can be produced by a variety of art-known techniques. For example, such propeptides can be synthesized (e.g., chemically or recombinantly), isolated and purified, and tested for their ability to form complexes with mature GDF-8 or mature BMP-11 protein using the methods described herein or methods known in the art. Propeptides can be synthesized using standard protein chemistry techniques such as those described in Bodansky, M. *Principles of Peptide Synthesis*, Springer Verlag, Berlin (1993) and Grant G. A. (ed.), *Synthetic Peptides: A User's Guide*, W. H. Freeman and Company, New York (1992), the contents of which are incorporated herein by reference. In addition, automated peptide synthesizers are commercially available (e.g., Advanced ChemTech Model 396; Milligen/Biosearch 9600).

Alternatively, the modified or unmodified GDF propeptides or fragments thereof may be recombinately produced using various expression systems (e.g., *E. coli*, Chinese Hamster Ovary cells, COS cells, baculovirus) as is well known in the art. For example, the expressed propeptide of GDF-8 or BMP-11 may be purified by, for example, using the method described in Bottinger et al. (1996) *PNAS* 93:5877–5882 and Gentry and Nash (1990) *Biochemistry* 29:6851–6857, the contents of which are incorporated herein by reference, or any other art recognized method for purifying peptides. Alternatively, the modified or unmodified GDF propeptide or fragment thereof may be tagged with, for example, FLAG or 6-His for subsequent purification using protein art-established techniques.

The modified or unmodified GDF-8 or BMP-11 propeptides may further be produced by digestion of naturally occurring or recombinantly produced GDF-8 or BMP-11 using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites. Alternatively, such GDF propeptides may be produced from naturally occurring or recombinantly produced GDF-8 or BMP-11 such as standard techniques known in the art, such as by chemical cleavage (e.g., cyanogen bromide, hydroxylamine).

The proteolytic or synthetic GDF-8 and BMP-11 propeptide portions of the modified GDF propeptide may comprise as many amino acid residues as are necessary to bind to the target GDF protein, thereby inhibiting, partially or completely, GDF-8 or BMP-11 activity. Examples 4–6, herein, illustrate embodiments of binding and inhibition assays. In particular, functional fragments of GDF-8 and/or BMP-11 propeptide sequences that maintain the ability to modulate or inhibit GDF-8, are included within the scope of the invention. The GDF-8 propeptide portions preferably comprise at least 5, 10, 20, 30, 40, 50, 60, 70, 80, or 90 amino acids; more preferably at least 100, 110, 120, 130, 140, 150, 160, 170, 180, or 190 amino acids; and most preferably at least 200, 210, 220, 230, or 240 or more amino acids in length. In a preferred embodiment, the GDF-8 propeptide portion of the modified GDF-8 propeptide is 243 amino acids in length, i.e., corresponding to SEQ ID NO:5; and the BMP-11 propeptide portion of the BMP-11 propeptide is 274 amino acids in length, i.e., corresponding to SEQ ID NO:11. The signal sequence for human GDF-8 is set forth in SEQ ID NO:13, and includes the first 23 amino acids of SEQ ID NO:1. In one embodiment, the sequence of BMP-11 propeptide begins with the amino acid sequence AEGPAAA (SEQ ID NO:19).

The signal sequence for human BMP-11 is set forth in SEQ ID NO.: 14 and includes the first 24 amino acids of SEQ ID NO.: 7. The identification of a partial GDF-8 or BMP-11 propeptide sequence as a functional fragment of GDF-8 or BMP-11 propeptide may readily be determined, for example, using the assays described in Examples 4–6 herein.

In addition to truncated propeptide sequences, the propeptide variants herein specifically include GDF propeptides having point mutations or other modifications (including insertion, deletion, and substitution); so long as such variants contain one or more desired biological or inhibitory activities of a GDF propeptide. Such activity can be measured, for example, as described in Examples 4–6. Such modifications may be introduced into the molecule to enhance the activity, circulatory or storage half-life, or production of the GDF-8 or BMP-11 propeptide. For example, point mutations may be introduced into one or more proteolytic cleavage sites to prevent or inhibit proteolytic degradation of the modified GDF-8 propeptide in vivo. Computer analysis (using a commercially available software, e.g., MacVector, Omega, PCGene, Molecular Simulation, Inc.) can be used to identify proteolytic cleavage sites.

Accordingly, methods of making GDF propeptides of the invention specifically include, in addition to the wild-type cDNA coding sequences, cDNA coding sequences that encode the wild-type GDF propeptides but which differ in cDNA sequence from the wild-type GDF cDNA sequence due to the degeneracies of the genetic code or allelic variations (naturally-occurring base changes in the species population which may or may not result in an amino acid change). The invention also contemplates DNA sequences that hybridize under stringent hybridization conditions (in one embodiment as described in T. Maniatis et al. (1982) *Molecular Cloning* (*A Laboratory Manual*), Cold Spring Harbor Laboratory, pp. 387–389) to a nucleic acid encoding a GDF propeptide or a nucleic acid encoding a protein or polypeptide having the ability to bind to a particular GDF protein, as embodied in Examples 4–6. Variations in the cDNA sequences caused by point mutations or by induced modifications (e.g., insertion, deletion, and substitution) to enhance the activity, half-life or production of the GDF-8 or BMP-11 propeptides encoded thereby are also useful for the present invention. Computer programs useful in the determination of DNA sequence homology are known in the art and are described herein.

The ability of a modified GDF propeptide to form a noncovalent complex with a GDF protein can be evaluated by a variety of methods known in the art, including size exclusion chromatography and/or cross linking analyses, as described in Example 2 herein. As shown in Example 2, the GDF-8 propeptide forms a noncovalent association with mature GDF-8 protein. The mature GDF-8/GDF-8 propeptide complex has an apparent molecular weight of approximately 75 kDa.

As stated above, in addition to the Fc fusion method, GDF propeptides may be stabilized by a number of other techniques. In one embodiment, a stabilizer portion is covalently linked to a GDF propeptide portion to create a fusion protein. For example, the GDF-8 propeptide may be linked to one or more of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337, incorporated by reference herein. In certain embodiments, GDF propeptides are chemically modified by covalent conjugation to a polymer to increase their circulating half-life. Preferred polymers, and methods to attach them to peptides, are also described in U.S. Pat. Nos. 4,766,106; 4,179,337; 4,495,285; and 4,609,546, incorporated by reference herein.

In another embodiment, the GDF-8 propeptide may be modified to have an altered glycosylation pattern (i.e., altered from the wild-type glycosylation pattern). As used herein, "altered" means having one or more carbohydrate moieties added or deleted, -to/from the wild-type GDF propeptide. Glycosylation of proteins and polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the GDF propeptide is conveniently accomplished by altering the amino acid sequence such that it contains or omits one or more of the above-described tripeptide sequences (for N-linked glycosylation sites). The alteration may also be made by the addition of, or substitution by, one or more serine or threonine residues to the sequence of the wild-type GDF propeptide (for O-linked glycosylation sites). For ease, the GDF propeptide amino acid sequence is preferably altered through changes at the DNA level, which techniques are well known in the art.

Another means of increasing the number of carbohydrate moieties on the GDF propeptide is by chemical or enzymatic coupling of glycosides to the GDF propeptide. These procedures are advantageous in that they do not require production of the GDF propeptide in a host cell that has glycosylation capabilities for N- or O-linked glycosylation. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published 11 Sep. 1987, and in Aplin and Wriston (1981) *CRC Crit. Rev. Biochem.*, pp. 259–306, incorporated by reference herein.

Removal of any carbohydrate moieties present on the GDF propeptide may be accomplished chemically or enzymatically. Chemical deglycosylation requires exposure of the GDF propeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact.

Chemical deglycosylation is described by Hakimuddin et al. (1987) *Arch. Biochem. Biophys.* 259:52 and by Edge et al. (1981) *Anal. Biochem.* 118:131. Enzymatic cleavage of carbohydrate moieties on GDF propeptides can be achieved by the use of a variety of endo- and exo-glycosidases as described by Thotakura et al. (1987) *Meth. Enzymol.* 138:350.

When the modified GDF propeptide is a GDF propeptide-Fc fusion protein, as described above, the Fc region of the IgG molecule may also be modified to have an altered glycosylation pattern.

In another embodiment, a GDF propeptide is linked to the protein albumin or a derivative of albumin. Methods for linking proteins and polypeptides to protein albumin or albumin derivatives are well known in the art. See e.g., U.S. Pat. No. 5,116,944 (Sivam et al.), incorporated by reference herein.

It is understood by one of ordinary skill in the art that certain amino acids may be substituted for other amino acids in a protein structure without adversely affecting the activity of the protein. It is thus contemplated by the inventors that various changes may be made in the amino acid sequences of the modified or unmodified GDF propeptides, or DNA sequences encoding such propeptides, without appreciable loss of their biological utility or activity. In one embodiment, such activity is measured in Examples 4–6. Such changes may include, but are not limited to, deletions, insertions, truncations, substitutions, fusions, and the like. For example, alterations of amino acid sequences at proteolytic cleavage sites within the modified GDF propeptide are explicitly encompassed within the present invention.

In making such changes, the hydropathic index of amino acids may be considered. The importance of the hydropathic amino acid index in conferring interactive biological function on a protein is generally understood in the art (Kyte and Doolittle (1982) J. Mol. Biol. 157:105–132). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, 1982, supra); these are isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (−4.5).

In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. For example, U.S. Pat. No. 4,554,101 states that the greatest local average hydrophilicity of a protein, as govern by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), serine (+0.3), asparagine (+0.2), glutamine (+0.2), glycine (−0), threonine (−0.4), proline (−0.5±1), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4).

In making such changes, the substitution of amino acids whose hydrophilicity values are within±2 is preferred, those which are within±1 are particularly preferred, and those within±0.5 are even more particularly preferred.

The modifications may be conservative such that the structure or biological function of the protein is not affected by the change. Such conservative amino acid modifications are based on the relative similarity of the amino acid side-chain substituents, for example, their hydrophobicity, hydrophilicity, charge, size, and the like. Exemplary conservative substitutions which take various of the foregoing characteristics into consideration are well known to those of skill in the art and include: arginine and lysine; glutamate and aspartate; serine and threonine; glutamine and asparagine; and valine, leucine, and isoleucine. The amino acid sequence of the modified GDF propeptides may be modified to have any number of conservative changes, so long as the binding of the modified GDF propeptide to its target GDF protein is not adversely affected.

Relative sequence similarity or identity (also known in the protein and molecular biology arts as sequence homology) is preferably determined using the "Best Fit" or "Gap" programs of the Sequence Analysis Software Package™ (Version 10; Genetics Computer Group, Inc., University of Wisconsin Biotechnology Center, Madison, Wis.). "Gap" utilizes the algorithm of Needleman and Wunsch (Needleman and Wunsch, 1970) to find the alignment of two sequences that maximizes the number of matches and minimizes the number of gaps. "BestFit" performs an optimal alignment of the best segment of similarity between two sequences. Optimal alignments are found by inserting gaps to maximize the number of matches using the local homology algorithm of Smith and Waterman (Smith and Waterman, 1981; Smith, et al., 1983).

The Sequence Analysis Software Package described above contains a number of other useful sequence analysis tools for identifying homologues of the presently disclosed nucleotide and amino acid sequences. For example, the "BLAST" program (Altschul, et al., 1990) searches for sequences similar to a query sequence (either peptide or nucleic acid) in a specified database (e.g., sequence databases maintained at the National Center for Biotechnology Information (NCBI) in Bethesda, Md., USA); "FastA" (Lipman and Pearson, 1985; see also Pearson and Lipman, 1988; Pearson, et al., 1990) performs a Pearson and Lipman search for similarity between a query sequence and a group of sequences of the same type (nucleic acid or protein); "TfastA" performs a Pearson and Lipman search for similarity between a protein query sequence and any group of nucleotide sequences (it translates the nucleotide sequences in all six reading frames before performing the comparison); "FastX" performs a Pearson and Lipman search for similarity between a nucleotide query sequence and a group of protein sequences, taking frameshifts into account. "TfastX" performs a Pearson and Lipman search for similarity between a protein query sequence and any group of nucleotide sequences, taking frameshifts into account (it translates both strands of the nucleic sequence before performing the comparison).

One of skill in the art will recognize that the modified or unmodified GDF propeptides may contain any number of substitutions to their amino acid sequences without altering their biological properties. In a preferred embodiment, such changes are conservative amino acid substitutions, that are well known in the art. Exemplary conservative substitutions which take various of the foregoing characteristics into consideration are well known to those of skill in the protein biochemistry art and include but are not limited to: arginine and lysine; glutamate and aspartate; serine and threonine; glutamine and asparagine; and valine, leucine, and isoleucine.

In certain embodiments of the invention, the in vivo stability of a protein can be measured in a number of ways. In one embodiment, serum or tissue samples are harvested at a variety of time points following delivery of the protein either intravenously or intraperitoneally or the protein is radiolabeled, i.e. with iodine-125, using methods well known to those in the art. The amount of radioactivity present in each serum or tissue sample can be determined using a gamma-counter. In another embodiment, the integrity/stability of the protein in the serum can be assessed by SDS-PAGE followed by either autoradiography or Western blot analysis. In another embodiment, the biological activity of the protein can be measured using any one of a number of functional assays, including an ELISA or cell-based assay known in the art.

Methods of Treating Disease

The GDF propeptides of the present invention are useful to prevent or treat various medical disorders in humans or animals. The GDF propeptides are preferably used to inhibit or reduce one or more activities associated with a GDF protein. In one highly preferred embodiment, the modified GDF propeptide inhibits or reduces one or more of the activities of mature GDF-8 relative to a mature GDF-8 protein that is not bound by the same propeptide. In a preferred embodiment, the activity of the mature GDF-8 protein, when bound by one or more of the modified GDF propeptides, is inhibited at least 50%, preferably at least 60, 62, 64, 66, 68, 70, 72, 74, 76, 78, 80, 82, 84, 86, or 88%, more preferably at least 90, 91, 92, 93, or 94%, and even more preferably at least 95% to 100% relative to a mature GDF-8 protein that is not bound by one or more of the modified GDF propeptides.

The medical disorder being treated or prevented by the modified GDF propeptides is preferably a muscle or neuromuscular disorder (such as amyotrophic lateral sclerosis, muscular dystrophy, muscle atrophy, congestive obstructive pulmonary disease, muscle wasting syndrome, sarcopenia, or cachexia), a metabolic disease (such as such as type 2 diabetes, noninsulin-dependent diabetes mellitus, hyperglycemia, or obesity), an adipose tissue disorder (such as obesity), or bone degenerative disease (such as osteoporosis). The medical condition is most preferably a muscle or neuromuscular disorder, such as amyotrophic lateral sclerosis, muscular dystrophy, muscle atrophy, congestive obstructive pulmonary disease, muscle wasting syndrome, sarcopenia, or cachexia. In another preferred embodiment, the medical condition is a metabolic disease or disorder, such as that resulting from dysfunctional glucose metabolism and/or insulin resistance, such as type 2 diabetes or noninsulin-dependent diabetes mellitus, or metabolic disorders such as hyperglycemia or obesity. The GDF propeptides are preferably used to prevent or treat such medical disorders in mammals, most preferably in humans.

The GDF propeptides or propeptides compositions of the present invention are administered in therapeutically effective amounts. As used herein, an "effective amount" of the modified GDF propeptide is a dosage which is sufficient to reduce the activity of GDF proteins to achieve a desired biological outcome (e.g., increasing skeletal muscle mass). In one embodiment, the desired biological outcome may be any therapeutic benefit including an increase in muscle mass, an increase in muscle strength, improved metabolism, decreased adiposity, or improved glucose homeostasis. Such improvements may be measured by a variety of methods including those that measure lean and fat body mass (such as duel x-ray scanning analysis), muscle strength, serum lipids, serum leptin, serum glucose, glycated hemoglobin, glucose tolerance, and improvement in the secondary complication of diabetes. Generally, a therapeutically effective amount may vary with the subject's age, weight, physical condition, and sex, as well as the severity of the medical condition in the subject. The dosage may be determined by a physician and adjusted, as necessary, to suit observed effects of the treatment. Generally, the compositions are administered so that GDF propeptides are given at a dose between 50 µg/kg and 20 mg/kg. Preferably, the GDF propeptides are given as a bolus dose, to maximize the circulating levels of GDF propeptides for the greatest length of time after the dose. Continuous infusion may also be used after the bolus dose.

The present invention also provides methods for preventing or treating metabolic diseases or disorders resulting from abnormal glucosehomeostasis. Normal glucose homeostasis requires, inter alia, the finely tuned orchestration of insulin secretion by pancreatic beta cells in response to subtle changes in blood glucose levels. One of the fundamental actions of insulin is to stimulate uptake of glucose from the blood into tissues, especially muscle and fat.

Accordingly, in one embodiment, the present invention provides a method for treating diabetes mellitus and related disorders, such as obesity or hyperglycemia, by administering to a subject a modified GDF propeptide or modified GDF propeptide composition in an amount sufficient to ameliorate the symptoms of the disease. Type 2 or noninsulin-dependent diabetes mellitus (NIDDM), in particular, is characterized by a triad of (1) resistance to insulin action on glucose uptake in peripheral tissues, especially skeletal muscle and adipocytes, (2) impaired insulin action to inhibit hepatic glucose production, and (3) dysregulated insulin secretion (DeFronzo, (1997) Diabetes Rev.5:177–269). Therefore, subjects suffering from type 2 diabetes can be treated according to the present invention by administration of a modified GDF propeptide, which increases sensitivity to insulin and glucose uptake by cells.

Similarly, other diseases and metabolic disorders characterized by insulin dysfunction (e.g., resistance, inactivity, or deficiency) and/or insufficient glucose transport into cells also can be treated according to the present invention by administration of a modified GDF propeptide, which increases sensitivity to insulin and glucose uptake by cells.

The modified GDF propeptide or modified GDF propeptide compositions of the present invention are administered in therapeutically effective amounts. When used for the treatment of diabetes and related disorders, an "effective amount" of the modified GDF propeptide is a dosage which is sufficient to reduce the activity of GDF proteins to achieve one or more desired therapeutic results, such as, for example, an increase in insulin sensitivity or glucose uptake by cells, a decrease in fat body mass or a desired change in serum lipids, serum leptin, serum glucose, glycated hemoglobin, glucose tolerance, or improvement in the secondary complication of diabetes. Generally, a therapeutically effective amount may vary with the subject's age, condition, and sex, as well as the severity of the insulin dysfunction in the subject. The dosage may be determined by a physician and adjusted, as necessary, to suit observed effects of the treatment. Generally, the compositions are administered so that GDF propeptides are given at a dose between 50 ug/kg and 20 mg/kg. Preferably, the GDF propeptides are given as a bolus dose, to maximize the circulating levels of GDF propeptides for the greatest length of time after the dose. Continuous infusion may also be used after the bolus dose.

The present invention also provides gene therapy for the in vivo production of GDF propeptides. Such therapy would achieve its therapeutic effect by introduction of the GDF propeptide polynucleotide sequences into cells or tissues having the disorders as listed above. Delivery of GDF propeptide polynucleotide sequences can be achieved using a recombinant expression vector such as a chimeric virus or a colloidal dispersion system. Especially preferred for therapeutic delivery of GDF propeptide polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated By inserting a GDF propeptide polynucleotide sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the GDF propeptide polynucleotide. In one preferred embodiment, the vector is targeted to muscle cells or muscle tissue.

Since recombinant retroviruses are defective, they require helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to .PSI.2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for GDF propeptide polynucleotide is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (See e.g., Fraley, et al., Trends Biochem. Sci., 6:77, 1981). Methods for efficient gene transfer using a lipsosome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine and distearoylphosphatidylcholine.

The targeting of liposomes is also possible based on, for example, organ-specificity, cell-specificity, and organelle-specificity and is known in the art.

The methods of treating or preventing the above medical conditions with the modified GDF propeptides can also be used to inhibit other proteins in the TGF-β1 superfamily. Many of these proteins are related in structure to GDF-8, such as BMP-11. Accordingly, in another embodiment, the invention provides methods of treating the aforementioned disorders by administering to a subject a modified GDF propeptide capable of inhibiting a non-GDF-8 protein, either alone or in combination with a modified GDF propeptide against GDF-8.

Modified GDF Propeptide Compositions

The present invention provides compositions comprising the modified GDF propeptides. Such compositions may be suitable for pharmaceutical use and administration to patients. The compositions typically comprise one or more modified GDF propeptides of the present invention and a pharmaceutically acceptable excipient. As used herein, the phrase "pharmaceutically acceptable excipient" includes any and all solvents, dispersion media, coatings, antibacterial and antifungal agents, isotonic and absorption delaying agents, and the like, that are compatible with pharmaceutical administration. The use of such media and agents for pharmaceutically active substances is well known in the art. Exemplary pharmaceutically acceptable excipients can be found in "The Handbook of Pharmaceutical Excipients" $3^{rd}$ Ed. 2000, Am. Pharmaceutical Press, A. E. Kibbe, ed. The compositions may also contain other active compounds providing supplemental, additional, or enhanced therapeutic functions. The pharmaceutical compositions may also be included in a container, pack, or dispenser together with instructions for administration.

A pharmaceutical composition of the invention is formulated to be compatible with its intended route of administration. Methods to accomplish the administration are known to those of ordinary skill in the art. It may also be possible to obtain compositions which may be topically or orally administered, or which may be capable of transmission across mucous membranes. The administration may, for example, be intravenous (I.V.), intraperitoneal (I.P.), intramuscular (I.M.), intracavity, subcutaneous (S.C.) or transdermal. Preferred embodiments include I.V., I.P., I.M. and S.C. injection. In one preferred embodiment, the pharmaceutical compositions of the invention are administered intravenously.

Solutions or suspensions used for intradermal or subcutaneous application typically include one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The pH can be adjusted with acids or bases, such as hydrochloric acid or sodium hydroxide. Such preparations may be enclosed in ampoules, disposable syringes or multiple dose vials made of glass or plastic.

Pharmaceutical compositions suitable for injection include sterile aqueous solutions or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Oral compositions generally include an inert diluent or an edible carrier. For example, they can be enclosed in gelatin capsules or compressed into tablets. For the purpose of oral therapeutic administration, the GDF propeptides can be incorporated with excipients and used in the form of tablets, troches, or capsules. Pharmaceutically compatible binding agents, and/or adjuvant materials can be included as part of the composition. The tablets, pills, capsules, troches, and the like can contain any of the following ingredients, or compounds of a similar nature; a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the GDF propeptides may be delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The GDF propeptides may also be prepared in the form of suppositories (e.g., with conventional suppository bases such as cocoa butter and other glycerides) or retention enemas for rectal delivery.

In one embodiment, the modified GDF propeptides are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions containing the modified GDF propeptides can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. GDF propeptides which exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any modified GDF propeptide used in the present invention, the therapeutically effective dose can be estimated initially from cell culture assays. A dose may be formulated in animal models to achieve a circulating plasma concentration range that includes the $IC_{50}$ (i.e., the concentration of the test modified GDF propeptide which achieves a half-maximal inhibition of symptoms) as determined in cell culture. Levels in plasma may be measured, for example, by high performance liquid chromatography. The effects of any particular dosage can be monitored by a suitable bioassay. Examples of suitable bioassays include DNA replication assays, transcription-based assays, GDF protein/receptor binding assays, creatine kinase assays, assays based on the differentiation of preadipocytes, assays based on glucose uptake in adipocytes, and immunological assays.

The following examples provide preferred embodiments of the invention. One of ordinary skill in the art will recognize the numerous modifications and variations that may be performed without altering the spirit or scope of the present invention. Such modifications and variations are believed to be encompassed within the scope of the invention. The examples do not in any way limit the invention.

The entire contents of all references, patents and published patent applications cited throughout this application are herein incorporated by reference.

EXAMPLES

Example 1

Purification of GDF-8

Conditioned media from a selected cell line expressing recombinant human GDF-8 protein (mature GDF-8+GDF-8 propeptide) was acidified to pH 6.5 and applied to a 80×50 mm POROS HQ anion exchange column in tandem to a 80×50 mm POROS SP cation exchange column (Perseptive Biosystems). The flow through was adjusted to pH 5.0 and applied to a 75×20 mm POROS SP cation exchange column (Perseptive Biosystems) and eluted with a NaCl gradient. Fractions containing the GDF-8, as indicated by sodium dodecyl sulfate polyacrylamide gel electrophoresis (SDS-PAGE), were pooled, acidified with trifluoroacetic acid (TFA) to pH 2–3, then brought up to 200 ml with 0.1% TFA to lower the viscosity. The pool was then applied to a 250×21.2 mm $C_5$ column (Phenomenex) preceded by a 60×21.2 mm guard column (Phenomenex) and eluted with a TFA/$CH_3CN$ gradient, to separate mature GDF-8 from GDF-8 propeptide. Pooled fractions containing mature GDF-8 were concentrated by lyophilization to remove the acetonitrile and 20 ml of 0.1% TFA was added. The sample was then applied to a 250×10 mm $C_5$ column (Phenomenex) heated to 60° C. to aid in separation. This was repeated until further separation could no longer be achieved. Fractions containing mature GDF-8 were then pooled and brought up to 40% acetonitrile and applied to a 600×21.2 BioSep S-3000 size exclusion column (Phenomenex) preceded by a 60×21.2 guard column. Fractions containing purified mature GDF-8 were pooled and concentrated for use in subsequent experiments. Typical yields of the mature GDF-8 dimer was 0.33 mg of protein per liter of conditioned media.

$C_5$ column fractions containing GDF-8 propeptide were pooled, the acetonitrile was removed by evaporation, 20 ml of 0.1% TFA was added, and the sample was then injected onto the 250×10 mm $C_5$ column at 60° C. This was repeated until further separation could no longer be achieved. Fractions containing the GDF-8 propeptide were then pooled and brought up to 40% acetonitrile and applied to a 600×21.2 BioSep S-3000 size exclusion column (Phenomenex) preceded by a 60×21.2 guard column. Fractions containing the purified GDF-8 propeptide were pooled and concentrated for use in subsequent experiments. A typical yield of the GDF-8 propeptide was 0.24 mg protein per liter of conditioned media.

On SDS-PAGE, purified mature GDF-8 migrated as a broad band at 25 kDa under nonreducing conditions and 13 kDa under reducing conditions. A similar SDS-PAGE profile has been reported for murine GDF-8 (McPherron et al. (1997) *Nature* 387:83–90), and reflects the dimeric nature of the mature protein.

The apparent molecular weight of purified GDF-8 propeptide was 38 kDa under both reducing and nonreducing conditions. This indicates that the GDF-8 propeptide is monomeric. The difference between the apparent molecular weight and the predicted molecular weight of GDF-8 propeptide, ~26 kDa, may reflect the addition of carbohydrate, since its amino acid sequence contains a potential N-linked glycosylation site (McPherron et al. (1997) *Proc. Natl. Acad. Sci. USA* 94:12457–12461). Thus, the above process led to the production of purified and active mature GDF-8 dimer and GDF-8 propeptide.

Example 2

Characteristics of Purified Recombinant Human GDF-8

50 ug each of purified mature GDF-8 and purified GDF-8 propeptide were mixed and dialyzed into 50 mM sodium phosphate, pH 7.0, and chromatographed on a 300×7.8 mm BioSep S-3000 size exclusion column (Phenomenex). Molecular weight of the mature GDF-8/propeptide complex was determined from elution time, using molecular weight standards (Bio-Rad Laboratories, Hercules, Calif.) chromatographed on the same column.

When purified GDF-8 propeptide was incubated with purified mature GDF-8 at neutral pH, the two proteins appeared to complex, as indicated by the size exclusion profile. The primary protein peak eluted at 12.7 minutes had an estimated molecular weight of 78 kDa from molecular weight standards (Bio-Rad Laboratories, Hercules, Calif.) chromatographed on the same column. The size of the complex is most consistent with one dimer of the mature GDF-8 associating with two monomers of propeptide, thus forming a tetrameric complex.

To confirm this observation, a preparation containing both mature GDF-8 and GDF-8 propeptide was incubated with or without 100 mM 1-Ethyl 3-[3-dimethylaminopropyl]carbodiamide hydrochloride (EDC, Pierce) for 1 hour at room temperature, acidified with HCl to pH 2–3, and concentrated with a Micron-10 concentrator (Amicon) for SDS-PAGE, using a tricine buffered 10% acrylamide gel. Proteins were visualized by Coomassie blue staining. A band corresponding to a molecular weight of about 75 kD was observed only in the sample EDC was added and not in the control lane, confirming the presence of the GDF-8 mature/GDF-8 propeptide complex. This valides the assay as useful for measuring the activity and concentration of purified mature GDF-8 dimer.

Example 3

In Vitro Biological Activity of Purified GDF-8

To demonstrate the activity of GDF-8, a reporter gene assay (RGA) was developed using a reporter vector pGL3 $(CAGA)_{12}$ sequence coupled to luciferase. The CAGA sequence was previously reported to be a TGF-β-responsive sequence within the promoter of the TGF-β-induced gene, PAI-1 (Dennler et al. (1998) *EMBO J.* 17:3091–3100).

The reporter vector containing 12 CAGA boxes was made using the basic reporter plasmid, pGL3 (Promega Corporation, Madison, Wis., USA, Cat. No. E1751). The TATA box and transcription initiation site from the adenovirus major late promoter (−35/+10) was inserted between the BglII and HindIII sites. Oligonucleotides containing twelve repeats of the CAGA boxes AGCCAGACA were annealed and cloned into the XhoI site. The human rhabdomyosarcoma cell line, A204 (ATCC HTB-82), was transiently transfected with pGL3$(CAGA)_{12}$ using FuGENE 6 transfection reagent (Roche Diagnostics, Indianapolis, USA, Cat. No. 1814443). Following transfection, cells were cultured on 48-well plates in McCoy's 5A medium (Life Technologies, Rockville, Md., USA, Cat. No. 21500-079) supplemented with 2 mM glutamine, 100 U/ml streptomycin, 100 μg/ml penicillin and 10% fetal calf serum for 16 h. Cells were then treated with GDF-8, BMP-11 or activin in McCoy's 5A media with glutamine, streptomycin, penicillin and 1 mg/ml bovine serum albumin for 6 h at 37° C. Luciferase was quantified in the treated cells using the Luciferase Assay System (Promega Corporation, Madison, Wis., USA, Cat. No. E1483). The assay results are illustrated in FIG. 1. For GDF-8, results are expressed as mean±S.E. for three separate experiments. For BMP-11 and activin, results are representative of two separate experiments.

The results show that GDF-8 maximally activated the reporter construct 10-fold, with an $ED_{50}$ of 10 ng/ml GDF-8, indicating that the purified recombinant GDF-8 was biologically active. BMP-11 which is 90% identical to GDF-8 at the amino acid level (Gamer et al. (1999) *Dev. Biol.* 208: 222–232 and Nakashima et al. (1999) *Mech. Dev.* 80:185–189), and activin elicited a similar biological response, indicating that the reporter gene assay is a suitable assay to detect the in vitro biological activity of GDF-8, BMP-11 or activin.

Example 4

Binding Properties of Purified GDF-8

The GDF-8 latent complex was biotinylated at a ratio of 20 moles of EZ-link Sulfo-NHS-Biotin (Pierce, Rockford, Ill., USA, Cat. NO. 21217) to 1 mole of the GDF-8 complex for 2 hours on ice, inactivated with 0.5% TFA, and subjected to chromatography on a C4 Jupiter 250×4.6 mm column (Phenomenex) to separate mature GDF-8 from GDF-8 propeptide. Biotinylated mature GDF-8 fractions eluted with a TFA/$CH_3CN$ gradient were pooled, concentrated and quantitated by MicroBCA protein Assay Reagent Kit (Pierce, Rockford, Ill, USA, Cat. No. 23235).

Recombinant ActRIIB-Fc chimera (R&D Systems, Minneapolis, Minn., USA Cat. No. 339-RB/CF) was coated on 96-well flat-bottom assay plates (Costar, N.Y., Cat. No. 3590) at 1 μg/ml in 0.2 M sodium carbonate buffer overnight at 4° C. Plates were then blocked with 1 mg/ml bovine serum albumin and washed following standard ELISA protocol. 100 μl of biotinylated GDF-8 aliqouts at various concentrations were added to the blocked ELISA plate, incubated for 1 hr, washed, and the amount of bound GDF-8 was detected by Streptavidin-Horseradish peroxidase (SA-HRP, BD PharMingen, San Diego, Calif., USA, Cat. No. 13047E) followed by the addition of TMB (KPL, Gaithersburg, Md., USA, Cat. No. 50-76-04). Colorimetric measurements were done at 450 nM in a Molecular Devices microplate reader.

Figure 2:
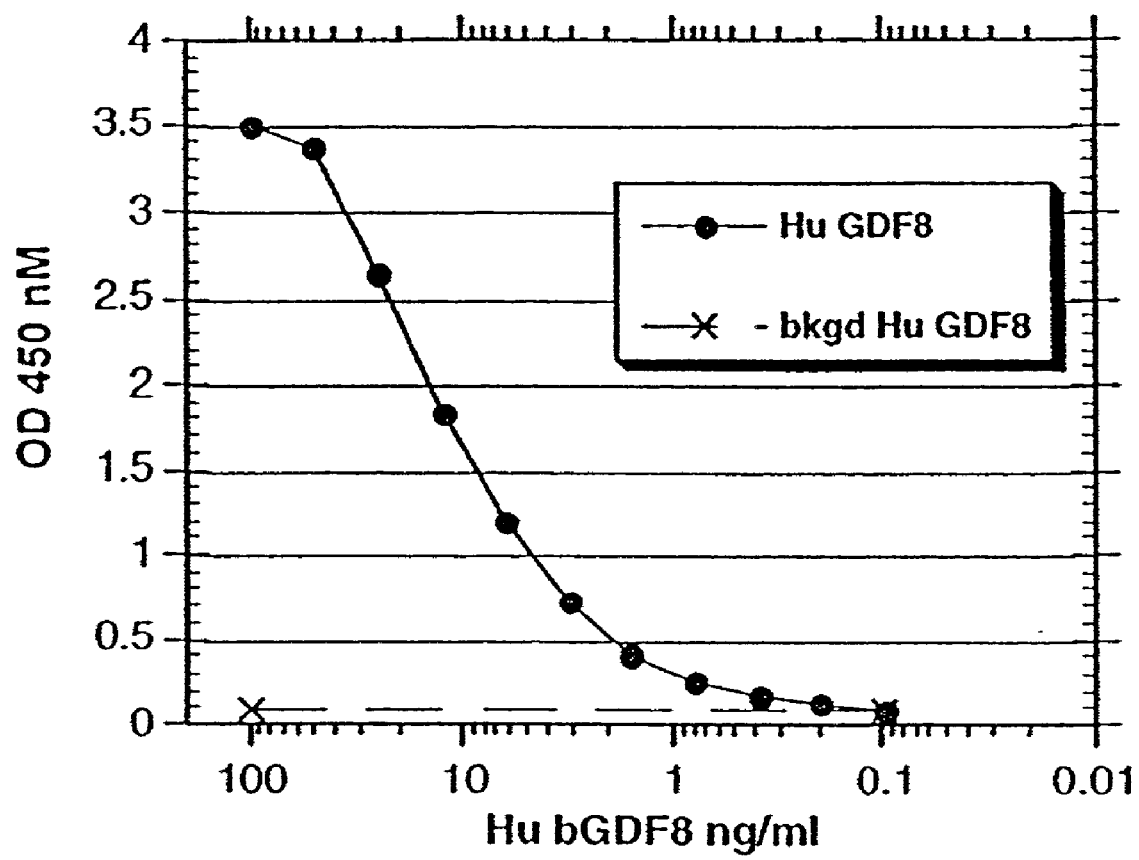
FIG. 2 shows the binding properties of purified biotinylated human GDF-8 in an ActRIIB binding assay.

As shown in FIG. 2, biotinylated GDF-8 bound to ActRIIB, the putative GDF-8 type II receptor with an $ED_{50}$ of 12 ng/ml, indicating that the ActRII binding assay is a sensitive in vitro binding assay for GDF-8.

Example 5

Inhibition of GDF-8 and BMP-11 by GDF-8 Propeptide

Figure 3:
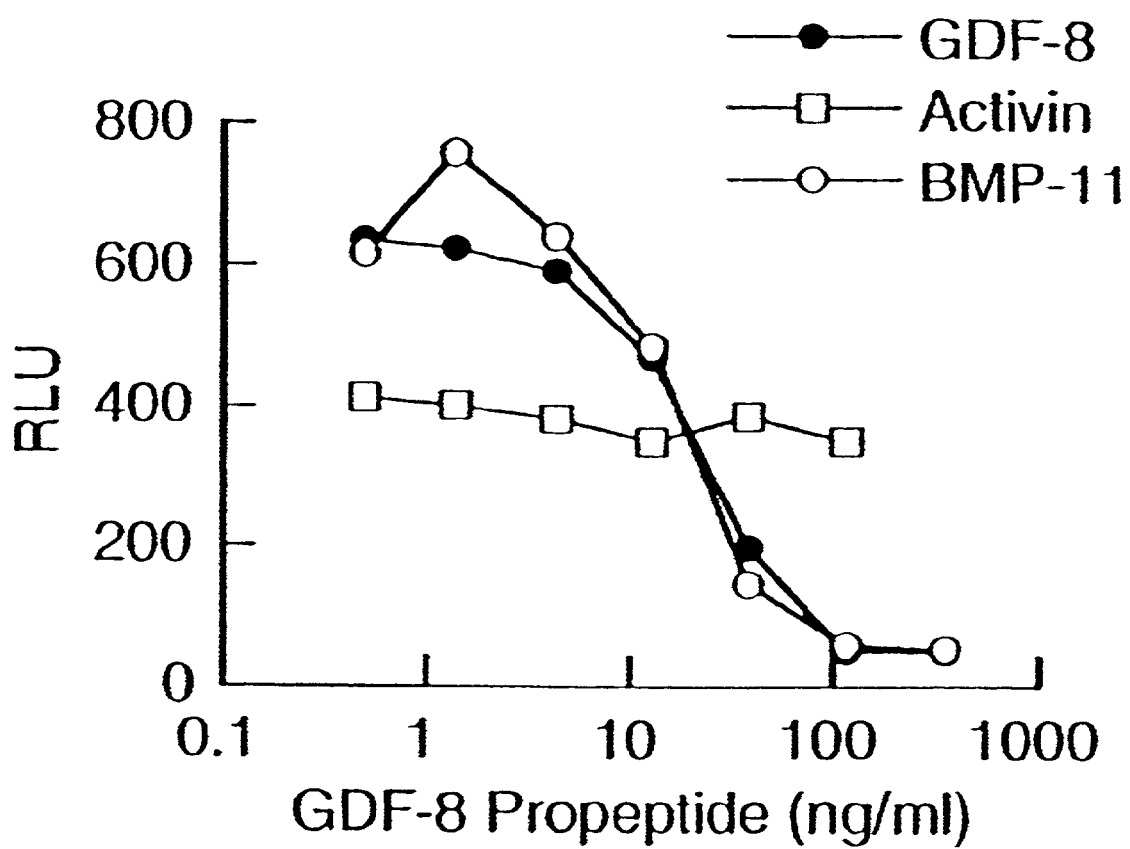
FIG. 3 shows induction of pGL3(CAGA)$_{12}$ reporter activity at the ED$_{50}$ for GDF-8, BMP-11, and activin in the presence of GDF-8 propeptide.

When GDF-8 was preincubated with GDF-8 propeptide for 1 hour at room temperature, the biological activity of GDF-8 was reduced. FIG. 3 shows induction of pGL3 $(CAGA)_{12}$ reporter activity at the $ED_{50}$ for GDF-8, 10 ng/ml, in the presence of GDF-8 propeptide. GDF-8 propeptide reduced the GDF-8 induction in a dose-responsive manner, with an $IC_{50}$ of 25 ng/ml (0.6 nM). GDF-8 propeptide also inhibited the biological activity of BMP-11 to the same extent. In contrast, the activity of activin in this assay was not affected by GDF-8 propeptide, presumably due to the relatively low homology between GDF-8 and activin, as compared to GDF-8 and BMP-11.

Figure 4:
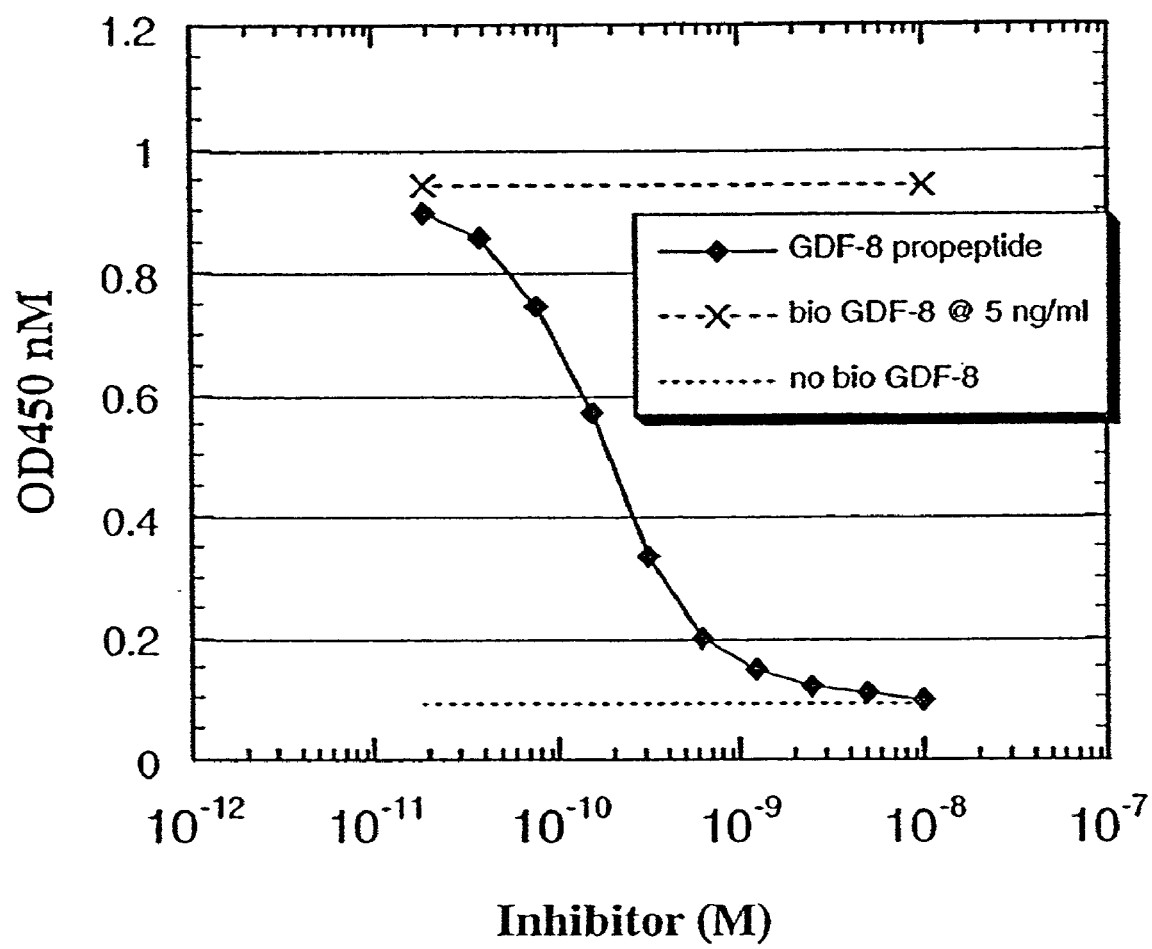
FIG. 4 shows the dose-dependent inhibition of biotinylated GDF-8 binding to ActRIIB by GDF-8 propeptide.

Likewise, FIG. 4 shows that preincubation of GDF-8 propeptide with the biotinylated GDF-8 at 5 ng/ml inhibited GDF-8 binding to ActRIIB in the ActRIIB binding assay, as described in Example 4, with an $IC_{50}$ of 0.3 nM. In conclusion, the GDF-8 propeptide of the invention is a potent subnanomolar inhibitor of GDF-8 and BMP-11 activity in vitro, as measured in the reporter gene assay and the ActRIIB binding assay. Accordingly, this assay shows that the GDF-8 propeptide is active and is a potent inhibitor of GDF-8 activity in this assay.

Example 6

Inhibition of GDF-8-Receptor Binding by GDF-8 Propeptide

GDF-8 was iodinated with chloramine T as described by Frolik et al. (1984) *J. Biol. Chem.* 259:10995–10999 to a specific activity of 100-200 μCi/μg. Iodinated-GDF-8 showed comparable biological activity to unlabeled GDF-8 in the $(CAGA)_{12}$ reporter assay described in Example 3. $^{125}$I-labeled GDF-8 was evaluated for specific binding to a myoblast cell line, L6.

L6 myoblast cells (ATCC CRL-1458) were grown to confluence in Dulbecco's modified Eagle's medium supplemented with 10% heat-inactivated fetal calf serum on gelatinized 24-well plates. Equilibrium binding was performed as described in Song et al. (1995) *Endocrinology* 136: 4293–4297, which is incorporated by reference in its entirety herein. 1 ng/ml $^{125}$I GDF-8 (with or without unlabeled GDF-8) was incubated with confluent L6 cells for 4 hours at 40° C. After washing cells, bound [$^{125}$I]GDF-8 was extracted and quantified with a gamma counter. Results are expressed as mean ±S.E. of triplicate determinations and are representative of three separate experiments.

Figure 5:
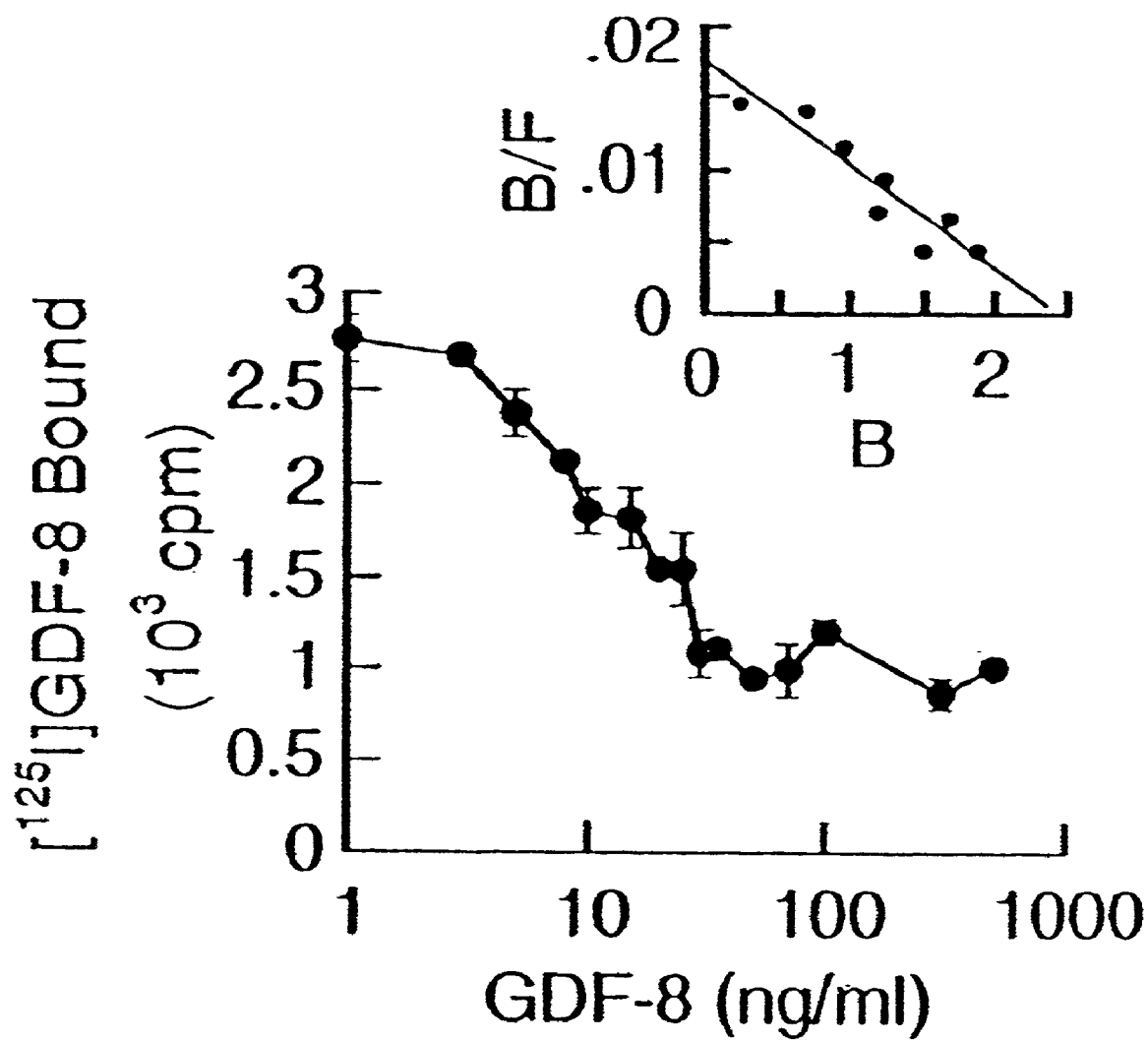
FIG. 5 shows the binding of GDF-8 to L6 cells.
Figure 6:
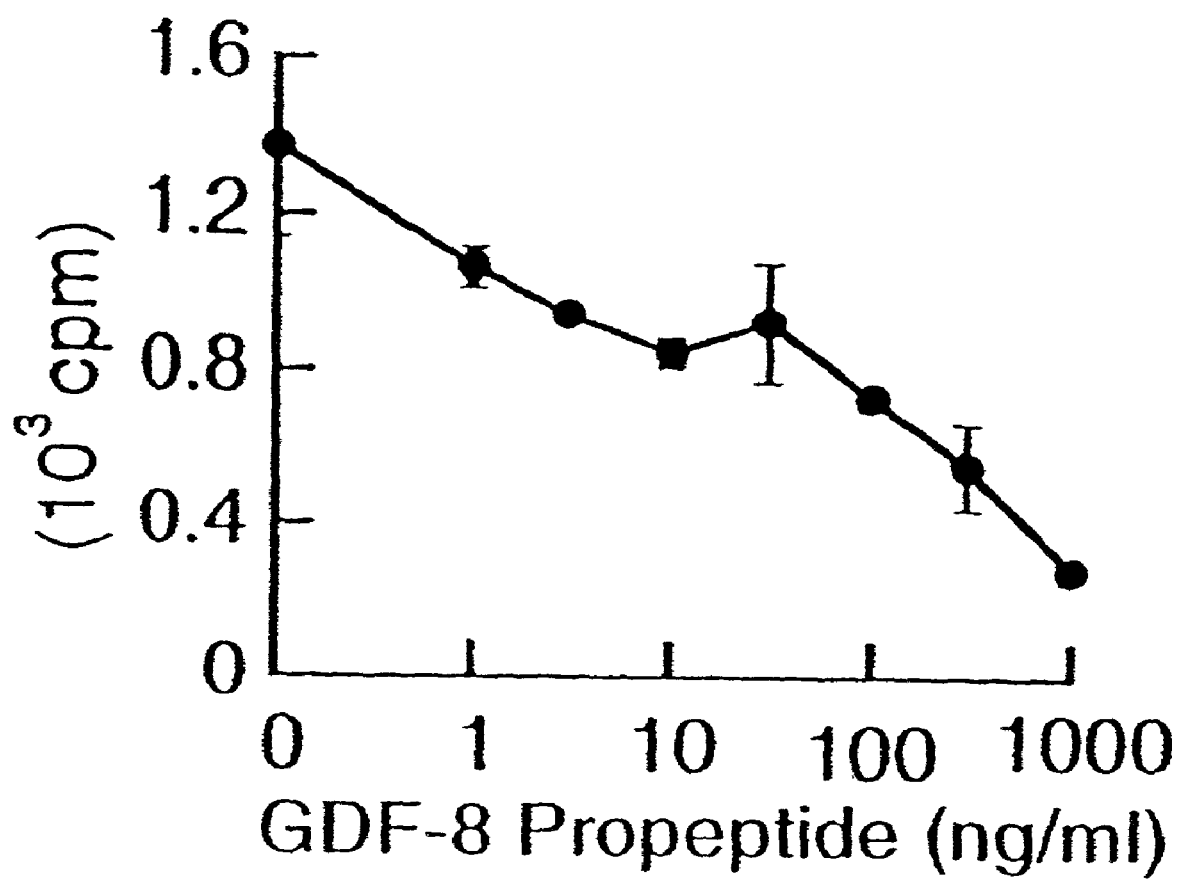
FIG. 6 shows the dose-dependent inhibition of GDF-8 specific binding to L6 cells by GDF-8 propeptide.

As shown in FIG. 5, $^{125}$I-GDF-8 bound to L6 cells with high affinity. Notably, BMP-11, but not TGF-β1, displaced $^{125}$I-GDF-8 binding, indicating that GDF-8 and BMP-11 (but not TGF-β1) share a common receptor on these cells (data not shown). From a Scatchard analysis of the GDF-8 binding, the $K_d$ was estimated to be 140 pM. Furthermore, when 1 ng/ml $^{125}$I-GDF-8 was preincubated with GDF-8 propeptide for 1 hour at room temperature, specific GDF-8 binding to L6 cells could be inhibited with increasing concentrations of unlabelled GDF-8 propeptide (FIG. 6). Results are expressed as mean±S.E. of triplicate determinations and are representative of two separate experiments. The $IC_{50}$ for 1 ng/ml GDF-8 was 140 ng/ml GDF-8 propeptide. As evidenced by these data, GDF-8 propeptide inhibits GDF-8 biological activity by blocking GDF-8 receptor binding.

Example 7

Inhibition of GDF-8 Activity by GDF-8 Propeptide-Fc Fusion Proteins

As shown in Example 8 below, murine GDF-8 propeptide has a relatively short in vivo half-life. To increase the bioavailability of the GDF-8 propeptide, fusions between the GDF-8 propeptide and a murine IgG2a Fc region were constructed using standard genetic engineering techniques.

Four mutations were introduced into the Fc region to reduce effector function, as described in Steurer et. al. (1995) *J. Immunol.* 155:1165–1174. Using standard PCR methodology, two fusion constructs were prepared by fusing a cDNA encoding the murine GDF-8 propeptide (amino acids 1-267) to the murine IgG2a Fc region (FIG. 7). Fusion 1 (FIG. 7A) encodes the first 265 amino acids of the murine GDF-8 propeptide (including a 24 amino acid secretory leader) fused in frame to 233 amino acids of the murine IgG2a Fc region starting at the first amino acid in the hinge section. Fusion 2 (FIG. 7B) is constructed in a manner similar to Fusion 1, except that a short glycine-serine-glycine-serine (GSGS) linker separates the GDF-8 propeptide from the murine Fc region.

Figure 8:
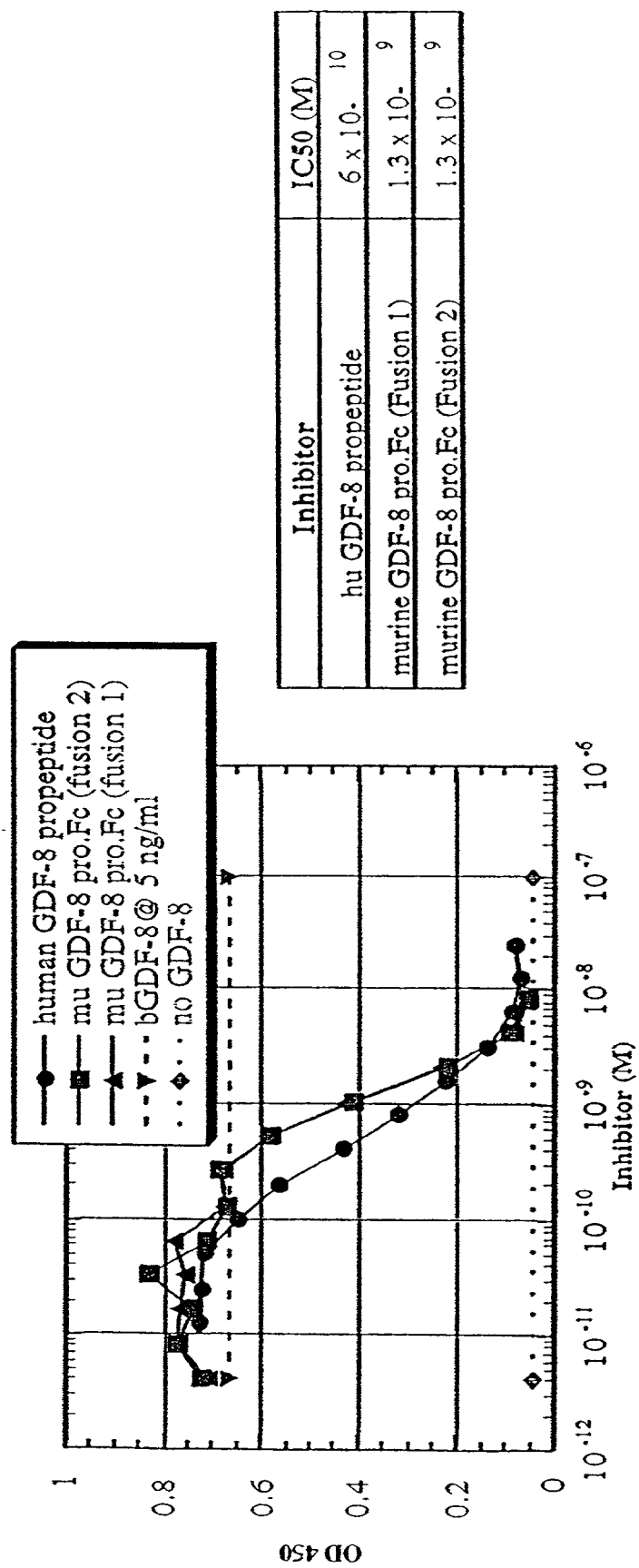
FIG. 8A shows the effects of human GDF-8 propeptide and two murine GDF-8 propeptide-Fc fusion proteins on GDF-8 binding in an ActRIIB competition ELISA.
FIG. 8B is a table comparing the IC$_{50}$'s of human GDF-8 propeptide and two murine GDF-8 propeptide-Fc fusion proteins.

The two chimera were introduced into an eukaryotic expression vector, pED (Kaufman et al. (1991) *Nucleic Acids Res.* 19:4485–4490) and transiently expressed in COS-1 M6 cells (Horowitz et al. (1983) *Journal of Molecular and Applied Genetics* 2:147–159), using Lipofectamine 2000 transfection reagent (Gibco BRL, Life Technologies, Rockville, Md., USA, Cat. No. 11668-019) according to manufacturer's protocol. After 24 hours incubation, R1CD1 (a modified DMEM/F12 serum-free culture medium) was added. Conditioned medium (CM) was pooled, fresh R1CD1 replaced, and CM was harvested again 60 hours later. Conditioned media was then pooled and purified over Protein A Sepharose CL-4B (Amersham Pharmacia Biotech, Buckinghamshire, HP7 9NA, England, Cat. No. 17-07080-01) after addition of $\frac{1}{10}^{th}$ volume of 1 M Tris pH 8.0. The purified protein was eluted in 0.1 M acetic acid, 150 mM NaCl and immediately neutralized with $\frac{1}{20}^{th}$ volume of 3M Tris pH 9.0. Proteins were quantitated using a standard murine IgG ELISA protocol, and assayed in the ActRIIB competition ELISA along with a purified human GDF-8 propeptide, as described in Example 5. The results are shown in FIG. 8. The $IC_{50}$'s of the GDF-8 propeptide-Fc fusions are in the low nanomolar range and there is no difference between fusion 1 and 2. Fusion 1 (no linker between GDF-8 propeptide and murine IgG2a) was selected for use in making a stable CHO cell line, and tested for inhibition of GDF-8 in the RGA assay.

The GDF-8 propeptide-Fc cDNA was subcloned into the CHO expression plasmid pHTop and transfected into CHO/A2 cells, as described in Thies et al. (2001) *Growth Factors* 18:251–259, which is incorporated by reference in its entirety herein. A stable cell line (PF-4/0.02) was established by selecting cells in 0.02 M methotrexate. Conditioned medium containing the GDF-8 propeptide-Fc fusion protein from a selected line was harvested and its pH was adjusted by addition of 10% v/v 1M Tris pH 8.0 and purified over Pharmacia rProteinA Sepharose Fast Flow (Amersham Pharmacia Biotech, Buckinghamshire, HP7 9NA, England, Cat. No. 17-1279-02) previously equilibrated with 50 mM Tris 150 mM NaCl pH 7.5. Fractions were eluted with 100 mM Acetic Acid, 150 mM NaCl pH 2.5 and immediately neutralized by adding 5% v/v 3M Tris pH 9.0. Peak fractions were pooled and loaded onto a Pharmacia Superdex 200 Size Exclusion Column (Amersham Pharmacia Biotech, Buckinghamshire, HP7 9NA, England, Cat. No. 17-1069-01). 0.05% Tween 80 was added to the fractions to prevent aggregation. Fractions were evaluated by SDS-PAGE on Novex 10% Tricine gels (Novex, San Diego, Calif., USA, Cat. No. EC66755).

Figure 9:
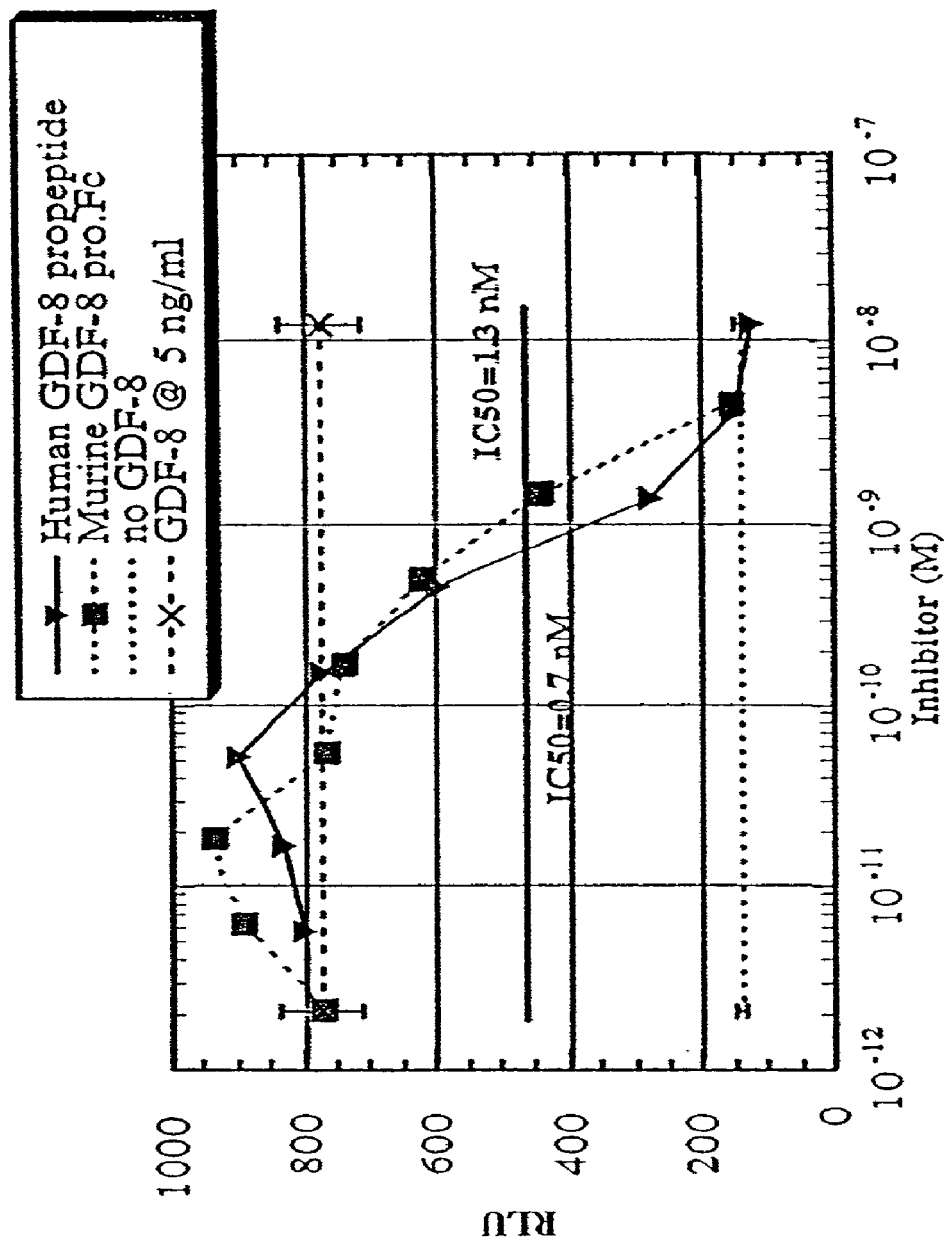
FIG. 9 shows the relative biological activities of human GDF-8 propeptide and murine GDF-8 propeptide-Fc fusion protein in a reporter gene assay.

Pooled fractions were quantitated by spectrophotometry and assayed for activity in the ActRIIB binding assay as described in Example 4, as well as in the reporter gene assay (FIG. 9). The $IC_{50}$ of the purified GDF-8 propeptide-Fc fusion was 1.3 nM. The data shows that the modified GDF propeptide of the invention comprising a GDF-8 propeptide-Fc fusion protein has retained potent inhibitory (neutralizing) activity compared to GDF-8 propeptide.

Example 8

Pharmacokinetics

Figure 10:
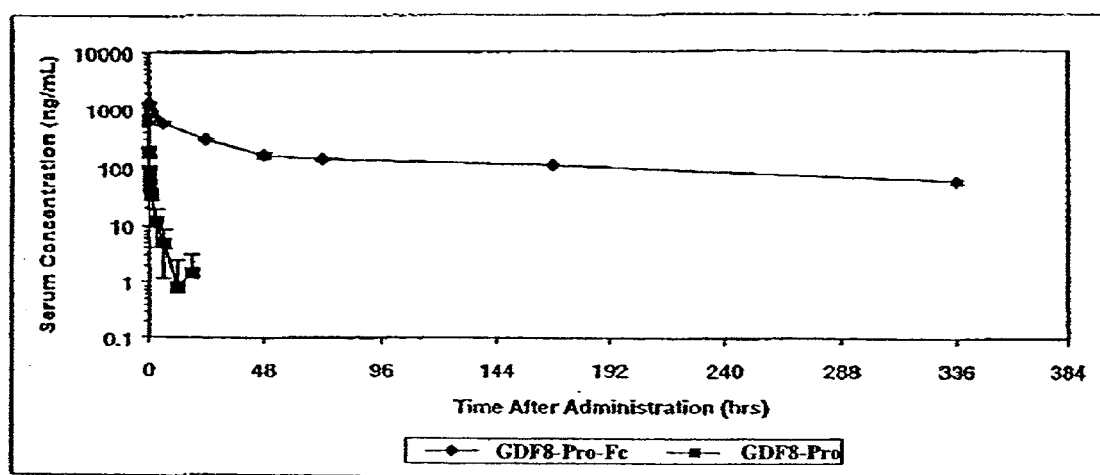
FIG. 10 shows the pharmacokinetics of iodinated GDF-8 propeptide and a GDF-8 propeptide-Fc fusion protein after a single intravenous administration of 0.2 µg/mouse or 2 µg/mouse, respectively.

The pharmacokinetics (PK) of GDF-8 propeptide (referred to herein as "GDF8-Pro") and GDF-8 propeptide-Fc fusion protein (referred to herein as "GDF8-ProFc") were evaluated in C57B1/6J mice at a dose of 0.2 ug/mouse (GDF8-Pro) or 2 ug/mouse (GDF8-ProFc) after a single intravenous administration. The animals received a mixture of unlabelled and $^{125}$I-labeled-GDF8-Pro or GDF8-ProFc at the doses listed above and serum concentrations were determined based on $I^{125}$ radioactivity in the serum and the specific activity of the injected dose. FIG. 10 shows the serum concentration versus time curves for both the GDF8-Pro and GDF8-ProFc. Table 1 shows the PK parameters for GDF8-Pro and GDF8-ProFc after a single intravenous administration of 2 µg/mouse. The serum concentrations and PK parameters for the GDF8-Pro are normalized to a dose of 2 µg/mouse for comparative purposes.

TABLE 1

|  | T½ (hrs) | Cmax (ng/mL) | Clearance (mL/hr) | MRT (hrs) | V1 (mL) | Vss (mL) |
| --- | --- | --- | --- | --- | --- | --- |
| GDF8-ProFc | 232 | 1392 | 0.03 | 286 | 1.4 | 8.7 |
| GDF-8-Pro | 2.2 | 390 | 12.4 | 2.3 | 5.1 | 28.3 |

T½: half life during the terminal elimination phase.
$C_{max}$: peak serum concentration
MRT: mean residence time
$V_1$: initial volume of distribution
$V_{SS}$: volume of distribution at steady state
Note: GDF8-Pro PK parameters normalized to a dose of 2 µg/mouse.

As can be seen in FIG. 10, the clearance is 400-fold slower, and the half-life is 100-fold longer for the GDF8-ProFc as compared to the GDF8-Pro. Both the initial volume of distribution and the volume of distribution at steady state are approximately 3-fold greater for the GDF8-Pro compared to the GDF8-ProFc, indicating that the GDF8-Pro distributes to a larger extent outside the vascular space compared to the GDF8-ProFc.

Although the stabilizing effect of the Fc region of an IgG molecule on a GDF propeptide is exemplified using the mouse GDF propeptide-Fc fusion protein (i.e., both components derived from mouse), the methods of the present invention can be applied to any combination of GDF propeptide and IgG components, regardless of the particular precursor protein or animal species from which the components are derived, provided the fusion protein is properly constructed to retain activity (i.e., as described herein).

Example 9

Derivation and Activity of Two Human GDF-8 Propeptide Fc Fusions

Two GDF-8 propeptide-Fc fusion constructs were prepared, using standard PCR methodology, for evaluation of therapeutic potential. A cDNA encoding the human GDF-8 propeptide (SEQ ID NO:5) was fused to the human IgG1 Fc region (SEQ ID NO:15; FIG. 11A) or human IgG1 Fc modified for reduced effector function (SEQ ID NO: 16; FIG. 11B).

1. Human GDF-8 Propeptide-IgG1 wt Fc Fusion Protein (FIG. 11A):

The first 264 amino acids of the human GDF-8 propeptide (including amino acids 1-241 of SEQ ID NO.:5 and the 23-amino acid signal peptide as set forth in SEQ ID NO:13) were fused in frame with the 232 amino acids of the human IgG1 constant region, starting at the first amino acid in the hinge region (SEQ ID NO.:15).

2. Human GDF-8 Propeptide-IgG1 Mutant (FIG. 11B):

The first 264 amino acids of the human GDF-8 propeptide, as described above, were fused in frame with the 227 amino acids of a mutated human IgG1 Fc region (SEQ ID NO.: 16). Two mutations, alanine residues (Ala-14 and Ala-17) at set forth in SEQ ID. NO.: 16 were introduced in order to reduce effector function as described in Lund et al. (1991) *J. Immun.* 147:2657–2662 and Morgan et al. (1995) *Immunology* 86:319–324.

Figure 12:
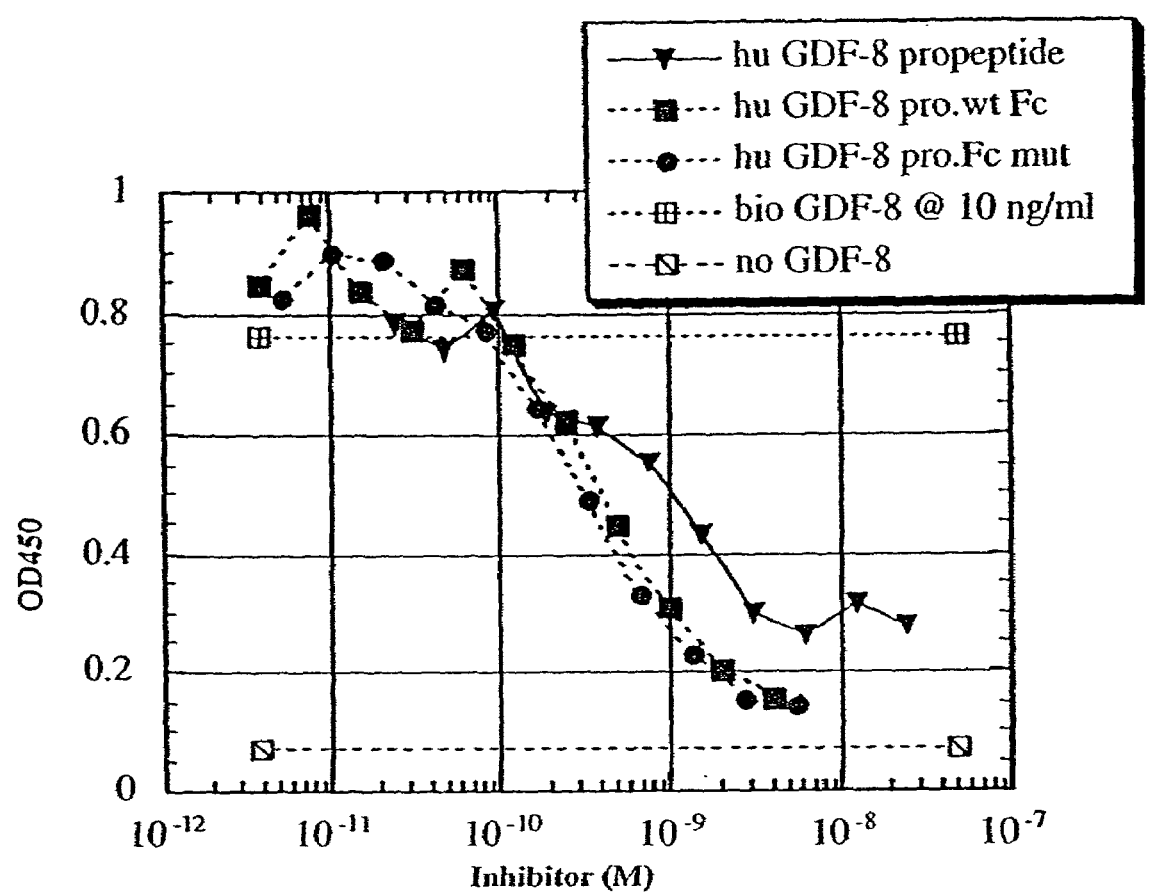
FIG. 12 shows the dose-dependent inhibition of GDF-8 binding in an ActRIIB competition ELISA by human GDF-8 propeptide and two human GDF-8 propeptide-Fc fusion proteins.

The two fusion proteins were introduced into an eukaryotic expression vector, pED (Kaufman et al. (1991) *Nucleic Acids Res.* 19:4485–4490) and transiently expressed in COS-1 M6 cells (Horowitz et al. (1983) *Journal of Molecular and Applied Genetics* 2:147–159), using Lipofectamine 2000 transfection reagent (Gibco BRL, Life Technologies, Rockville, Md., USA, Cat. No. 11668-019) according to manufacturer's protocol. After 24 hours incubation, R1CD1 (a modified DMEM/F12 serum-free culture medium) was added. Conditioned medium (CM) was pooled, fresh R1CD1 replaced, and CM was harvested again 60 hours later. Conditioned media was then pooled and purified over Protein A Sepharose CL-4B (Amersham Pharmacia Biotech, Buckinghamshire, HP7 9NA, England, Cat. No. 17-07080-01) after addition of $1/10^{th}$ volume of 1 M Tris pH 8.0. The purified protein was eluted in 0.1 M acetic acid, 150 mM NaCl and immediately neutralized with $1/20^{th}$ volume of 3M Tris pH 9.0. Proteins were quantitated using a standard human IgG ELISA protocol, and assayed in the ActRIIB binding assay along with a purified human GDF-8 propeptide, as described in Example 5. The results are shown in FIG. 12. In conclusion, both human propeptide-Fc fusion proteins are potent inhibitors of GDF-8 binding to ActRIIB.

Example 10

In Vivo Testing of GDF-8 Propeptide-Fc Fusion Protein

Figure 13:
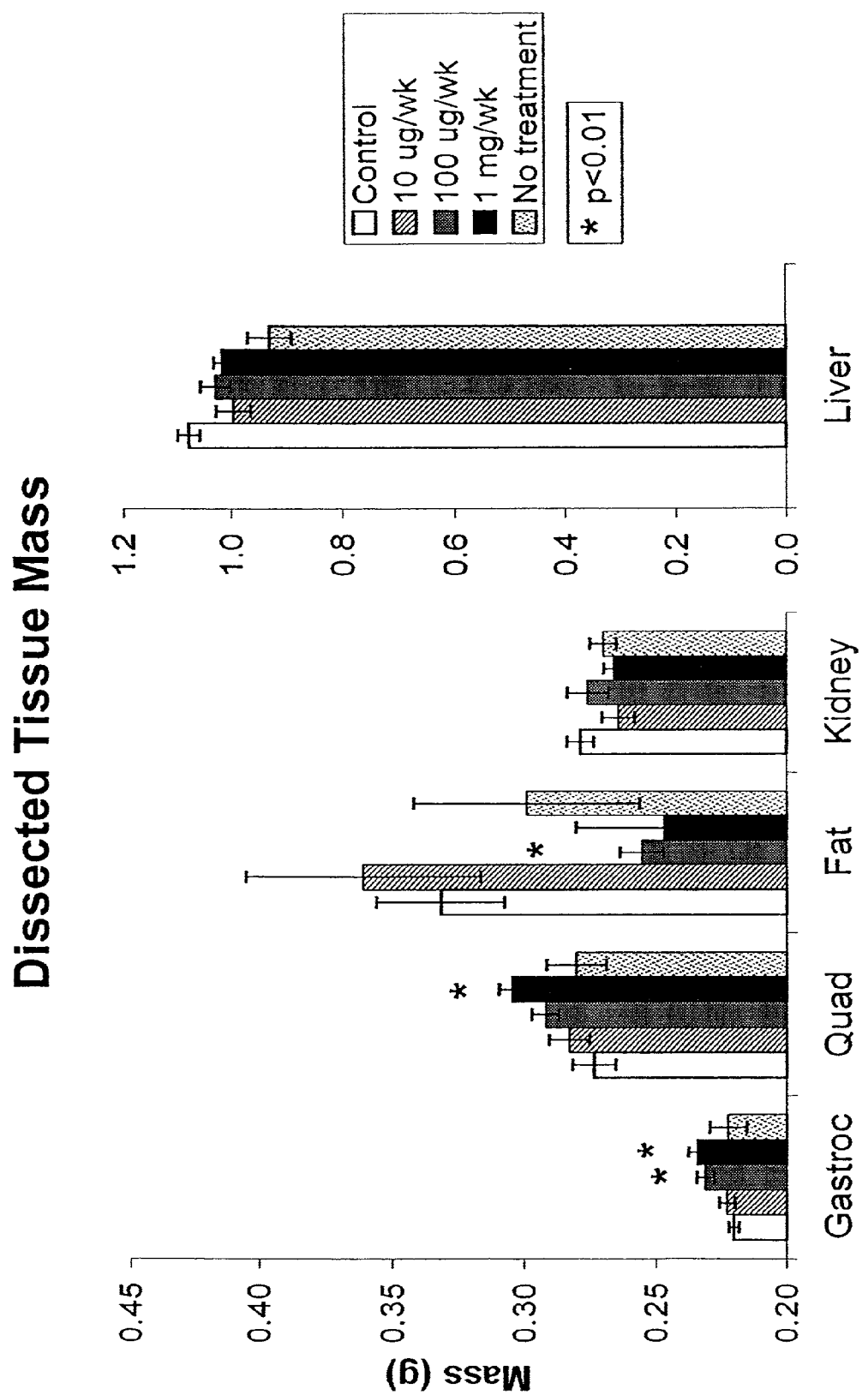
FIG. 13 is a graph showing that modified GDF-8 propeptide administered in vivo increases gastrocnemius and quadricep mass, and decreases fat mass, but does not effect kidney or liver mass compared to untreated mice or mice treated with the control protein, IgG2aFc.

The murine GDF-8 propeptide-Fc fusion protein (from Example 9) was tested in adult mice. Seven to nine week old, adult, female BALB/c mice were randomized with respect to body weight and placed into groups of seven (except for the no treatment group, which had six mice). Mice were dosed twice weekly by I.P. injection with a total weekly dose of 10 ug, 100 ug, or 1000 ug per animal for five weeks. Control injections were murine IgG2a-Fc at a molar equivalent to the high dose of propeptide-Fc. At the end of the study, gastrocnemius, quadriceps, epididymal fat pad, kidney, and liver were removed and weighed. FIG. 13 shows the average tissue mass, with the error bars indicating the standard error of the mean. The asterisk (*) indicates a statistically significant difference ($p<0.01$ using a students T test) when compared with the mice treated with the control protein, IgG2aFc. Blocking GDF-8 activity in vivo by I.P. injection of GDF-8 propeptide-Fc fusion protein at 1 mg/week (treated mice) resulted in a 6.2% increase in gastrocnemius and 11.3% increase in quadricep muscle mass compared to control mice not receiving GDF-8 propeptide-Fc fusion protein. In addition, blocking GDF-8 activity in vivo by I.P. injection of GDF-8 propeptide-Fc fusion protein at 100 ug/week (treated mice) results in 23.0% increase in fat pad mass. The high dose (1mg/week) treatement also led to a decrease in fat pad mass, but due to the variability in pat pad mass, the difference was not highly statistically significant ($p=0.047$). There was no effect of treatment on the mass of other tissues tested, including liver and kidney. In summary, the modified GDF-8 propeptide blocked GDF-8 activity in vivo and lead to an increase in muscle mass and a decrease in fat mass. In summary, blocking GDF-8 activity in vivo by I.P. injection of GDF-8 propeptide-Fc fusion protein (treated mice) resulted in increased gastrocnemious and quadricep muscle mass compared to control mice not receiving GDF-8 propeptide-Fc fusion protein.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A GDF-8 propeptide that has been modified at the aspartate residue corresponding to Asp 76 of SEQ ID NO:5 comprising
an amino acid sequence that is at least 95% identical to SEQ ID NO:5,
wherein the modification is a mutation at aspartate 76 of SEQ ID NO:5, and
wherein the GDF-8 propeptide has an increased in vivo or in vitro half-life relative to a corresponding unmodified GDF-8 propeptide; and
wherein the 8 propeptide inhibits one or more GDF-8 activities chosen from GDF-8 propeptide binding, negative regulation of skeletal muscle mass, modulation of preadipocyte differentiation, inhibition of muscle formation, inhibition of muscle cell growth, inhibition of muscle development, regulation of muscle-specific enzymes, inhibition of myoblast cell proliferation, modulation of preadipocyte differentiation to adipocytes, increasing sensitivity to insulin, regulation of glucose uptake, glucose hemostasis, and modulation of neuronal cell development and maintenance.

2. The GDF-8 propeptide of claim 1, wherein the residue corresponding to position 76 of SEQ ID NO:5 is alanine.

3. The GDF-8 propeptide of claim 1 further comprising an Fc region of an IgG molecule.

4. The GDF-8 propeptide of claim 3, wherein the IgG molecule is IgG1 or IgG4.

5. The GDF-8 propeptide of claim 3, wherein the amino acid sequence of the IgG molecule is SEQ ID NO:16.

6. The GDF-8 propeptide of claim 3, wherein the GDF-8 propeptide portion is fused to the Fc region of the IgG molecule via a linker peptide.

7. The GDF-8 propeptide of claim 3, further comprising an altered glycosylation site.

8. The GDF-8 propeptide of claim 3, further comprising at least one carbohydrate moiety.

9. The GDF-8 propeptide of claim 1, further comprising albumin.

10. The GDF-8 propeptide of claim 1, further comprising a nonproteinaceous polymer.

11. The GDF-8 propeptide of claim 1, further comprising a second moiety.

12. The GDF-8 propeptide of claim 11, wherein the second moiety is chosen from a protein, polypeptide, carbohydrate, and nonproteinaceous polymer.

13. The GDF-8 propeptide of claim 1, wherein the GDF-8 propeptide further comprises an immunoglobulin molecule, or a fragment thereof.

14. A pharmaceutical composition comprising the GDF-8 propeptide of claim 1 and a pharmaceutically acceptable excipient.

15. A GDF-8 propeptide that has been modified at the aspartate residue corresponding to Asp 76 of SEQ ID NO:5 comprising a non-human GDF-8 propeptide homolog of SEQ ID NO:5 chosen from bovine, chicken, murine, rat, porcine, ovine, turkey, baboon, and fish,
wherein the modification is a mutation at the aspartate corresponding to position 76 of SEQ ID NO:5,
wherein the GDF-8 propeptide has an increased in vivo or in vitro half-life; and
wherein the GDF-8 propeptide inhibits one or more GDF-8 activities chosen from GDF-8 propeptide binding, negative regulation of skeletal muscle mass, modulation of preadipocyte differentiation, inhibition of muscle formation, inhibition of muscle cell growth, inhibition of muscle development, regulation of muscle-specific enzymes, inhibition of myoblast cell proliferation, modulation of preadipocyte differentiation to adipocytes, increasing sensitivity to insulin, regulation of glucose uptake, glucose hemostasis, and modulation of neuronal cell development and maintenance.

16. A GDF-8 propeptide comprising an amino acid sequence that is at least 95% identical to SEQ ID NO:5, wherein the GDF-8 propeptide has a mutation at aspartate 76 of SEQ ID NO:5, wherein the mutation increases the in vivo or in vitro half-life of the GDF-8 propeptide, and wherein the GDF-8 propeptide inhibits a GDF-8 activity associated with negative regulation of skeletal muscle mass.

17. The GDF-8 propeptide according to any one of claims 1, 15, and 16, wherein the mutation that modifies the aspartate residue corresponding to Asp 76 of SEQ ID NO:5 is a substitution mutation.

18. The GDF-8 propeptide according to any one of claims 1, 15, and 16, wherein the mutation that modifies the aspartate residue corresponding to Asp 76 of SEQ ID NO:5 is an insertion mutation.

19. The GDF-8 propeptide according to any one of claims 1, 15, and 16, wherein the mutation that modifies the aspartate residue corresponding to Asp 76 of SEQ ID NO:5 is a deletion mutation.

20. The GDF-8 propeptide according to any one of claims 1, 15, and 16, wherein the mutation inactivates a proteolytic cleavage site.

* * * * *

SEQUENCE LISTING

```
<160> NUMBER OF SEQ ID NOS: 16

<210> SEQ ID NO 1
<211> LENGTH: 375
<212> TYPE: PRT
<213> ORGANISM: Homo sapiens

<400> SEQUENCE: 1

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60
```

-continued

```
Arg Leu Glu Thr Ala Pro Asn Ile Ser Lys Asp Val Ile Arg Gln Leu
 65                  70                  75                  80

Leu Pro Lys Ala Pro Pro Leu Arg Glu Leu Ile Asp Gln Tyr Asp Val
             85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
            115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
                180                 185                 190

Lys Leu Asp Met Asn Pro Gly Thr Gly Ile Trp Gln Ser Ile Asp Val
            195                 200                 205

Lys Thr Val Leu Gln Asn Trp Leu Lys Gln Pro Glu Ser Asn Leu Gly
210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
                260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
                340                 345                 350

Phe Asn Gly Lys Glu Gln Ile Ile Tyr Gly Lys Ile Pro Ala Met Val
            355                 360                 365

Val Asp Arg Cys Gly Cys Ser
    370                 375
```

<210> SEQ ID NO 2
<211> LENGTH: 1125
<212> TYPE: DNA
<213> ORGANISM: Homo sapiens

<400> SEQUENCE: 2

```
atgcaaaaac tgcaactctg tgtttatatt tacctgtttta tgctgattgt tgctggtcca      60
gtggatctaa atgagaacag tgagcaaaaa gaaaatgtgg aaaagagggg gctgtgtaat     120
gcatgtactt ggagacaaaa cactaaatct tcaagaatag aagccattaa gatacaaatc     180
ctcagtaaac ttcgtctgga acagctcct aacatcagca agatgttat aagacaactt       240 ttacccaaag ctcctccact ccgggaactg attgatcagt atgatgtcca gagggatgac     300
agcagcgatg gctctttgga agatgacgat tatcacgcta caacggaaac aatcattacc     360
```

```
atgcctacag agtctgattt tctaatgcaa gtggatggaa acccaaatg ttgcttcttt      420 aaatttagct ctaaaataca atacaataaa gtagtaaagg cccaactatg gatatatttg    480
agacccgtcg agactcctac aacagtgttt gtgcaaatcc tgagactcat caaacctatg    540
aaagacggta caaggtatac tggaatccga tctctgaaac ttgacatgaa cccaggcact    600
ggtatttggc agagcattga tgtgaagaca gtgttgcaaa attggctcaa acaacctgaa    660
tccaacttag gcattgaaat aaaagcttta gatgagaatg gtcatgatct tgctgtaacc    720
ttcccaggac aggagaaga tgggctgaat ccgttttag aggtcaaggt aacagacaca      780
ccaaaaagat ccagaaggga ttttggtctt gactgtgatg agcactcaac agaatcacga    840
tgctgtcgtt accctctaac tgtggatttt gaagcttttg gatgggattg gattatcgct    900
cctaaaagat ataaggccaa ttactgctct ggagagtgtg aatttgtatt tttacaaaaa    960
tatcctcata ctcatctggt acaccaagca aaccccagag gttcagcagg cccttgctgt    1020
actcccacaa agatgtctcc aattaatatg ctatatttta atggcaaaga acaaataata    1080
tatgggaaaa ttccagcgat ggtagtagac cgctgtgggt gctca                   1125

<210> SEQ ID NO 3
<211> LENGTH: 109
<212> TYPE: PRT
<213> ORGANISM: Homo sapiens

<400> SEQUENCE: 3

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
                20                  25                  30

Ile Ala Pro Lys Arg Tyr Lys Ala Asn Tyr Cys Ser Gly Glu Cys Glu
            35                  40                  45

Phe Val Phe Leu Gln Lys Tyr Pro His Thr His Leu Val His Gln Ala
        50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 4
<211> LENGTH: 327
<212> TYPE: DNA
<213> ORGANISM: Homo sapiens

<400> SEQUENCE: 4
gattttggtc ttgactgtga tgagcactca acagaatcac gatgctgtcg ttaccctcta     60
actgtggatt ttgaagcttt tggatgggat tggattatcg ctcctaaaag atataaggcc    120
aattactgct ctggagagtg tgaatttgta ttttacaaa aatatcctca tactcatctg     180
gtacaccaag caaaccccag aggttcagca ggcccttgct gtactcccac aaagatgtct    240
ccaattaata tgctatattt taatggcaaa gaacaaataa tatatgggaa aattccagcg    300
atggtagtag accgctgtgg gtgctca                                         327

<210> SEQ ID NO 5
<211> LENGTH: 243
```

```
<212> TYPE: PRT
<213> ORGANISM: Homo sapiens

<400> SEQUENCE: 5

Asn Glu Asn Ser Glu Gln Lys Glu Asn Val Glu Lys Glu Gly Leu Cys
1               5                   10                  15

Asn Ala Cys Thr Trp Arg Gln Asn Thr Lys Ser Ser Arg Ile Glu Ala
            20                  25                  30

Ile Lys Ile Gln Ile Leu Ser Lys Leu Arg Leu Glu Thr Ala Pro Asn
        35                  40                  45

Ile Ser Lys Asp Val Ile Arg Gln Leu Leu Pro Lys Ala Pro Pro Leu
    50                  55                  60

Arg Glu Leu Ile Asp Gln Tyr Asp Val Gln Arg Asp Ser Ser Asp
65                  70                  75                  80

Gly Ser Leu Glu Asp Asp Asp Tyr His Ala Thr Thr Glu Thr Ile Ile
                85                  90                  95

Thr Met Pro Thr Glu Ser Asp Phe Leu Met Gln Val Asp Gly Lys Pro
            100                 105                 110

Lys Cys Cys Phe Phe Lys Phe Ser Ser Lys Ile Gln Tyr Asn Lys Val
        115                 120                 125

Val Lys Ala Gln Leu Trp Ile Tyr Leu Arg Pro Val Glu Thr Pro Thr
    130                 135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Asn Pro Gly
                165                 170                 175

Thr Gly Ile Trp Gln Ser Ile Asp Val Lys Thr Val Leu Gln Asn Trp
            180                 185                 190

Leu Lys Gln Pro Glu Ser Asn Leu Gly Ile Glu Ile Lys Ala Leu Asp
        195                 200                 205

Glu Asn Gly His Asp Leu Ala Val Thr Phe Pro Gly Pro Gly Glu Asp
    210                 215                 220

Gly Leu Asn Pro Phe Leu Glu Val Lys Val Thr Asp Thr Pro Lys Arg
225                 230                 235                 240

Ser Arg Arg

<210> SEQ ID NO 6
<211> LENGTH: 729
<212> TYPE: DNA
<213> ORGANISM: Homo sapiens

<400> SEQUENCE: 6
aatgagaaca gtgagcaaaa agaaaatgtg gaaaagagg ggctgtgtaa tgcatgtact    60
tggagacaaa acactaaatc ttcaagaata gaagccatta agatacaaat cctcagtaaa   120
cttcgtctgg aaacagctcc taacatcagc aaagatgtta tagcaacact tttacccaaa   180
gctcctccac tccgggaact gattgatcag tatgatgtcc agagggatga cagcagcgat   240 ggctcttttgg aagatgacga ttatcacgct acaacgaaaa caatcattac catgcctaca   300
gagtctgatt ttctaatgca agtggatgga aaacccaaat gttgcttctt taaatttagc   360
tctaaaatac aatacaataa agtagtaaag gcccaactat ggatatattt gagacccgtc   420
gagactccta caacagtgtt tgtgcaaatc ctgagactca tcaaacctat gaaagacggt   480
acaaggtata ctggaatccg atctctgaaa cttgacatga acccaggcac tggtatttgg   540
cagagcattg atgtgaagac agtgttgcaa aattggctca acaacctga atccaactta   600
```

-continued

```
ggcattgaaa taaaagcttt agatgagaat ggtcatgatc ttgctgtaac cttcccagga    660
ccaggagaag atgggctgaa tccgttttta gaggtcaagg taacagacac accaaaaaga    720
tccagaagg                                                            729
```

<210> SEQ ID NO 7
<211> LENGTH: 407
<212> TYPE: PRT
<213> ORGANISM: Homo sapiens

<400> SEQUENCE: 7

```
Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
            20                  25                  30

Ala Ala Ala Ala Ala Ala Ala Ala Gly Val Gly Gly Glu Arg Ser
        35                  40                  45

Ser Arg Pro Ala Pro Ser Val Ala Pro Glu Pro Asp Gly Cys Pro Val
    50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
            100                 105                 110

Ile Leu Asp Leu His Asp Phe Gln Gly Asp Ala Leu Gln Pro Glu Asp
        115                 120                 125

Phe Leu Glu Glu Asp Glu Tyr His Ala Thr Thr Glu Thr Val Ile Ser
    130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
        195                 200                 205

Ala Gly Gly Gly Gly Gly Arg Arg His Ile Arg Ile Arg Ser Leu
    210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
        275                 280                 285

Val Leu Glu Asn Thr Lys Arg Ser Arg Arg Asn Leu Gly Leu Asp Cys
    290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
```

```
                   340                 345                 350
Tyr Pro His Thr His Leu Val Gln Gln Ala Asn Pro Arg Gly Ser Ala
            355                 360                 365

Gly Pro Cys Cys Thr Pro Thr Lys Met Ser Pro Ile Asn Met Leu Tyr
        370                 375                 380

Phe Asn Asp Lys Gln Gln Ile Ile Tyr Gly Lys Ile Pro Gly Met Val
385                 390                 395                 400

Val Asp Arg Cys Gly Cys Ser
                405

<210> SEQ ID NO 8
<211> LENGTH: 1221
<212> TYPE: DNA
<213> ORGANISM: Homo sapiens

<400> SEQUENCE: 8
atggtgctcg cggccccgct gctgctgggc ttcctgctcc tcgccctgga gctgcggccc      60
cggggggagg cggccgaggg ccccgcggcg gcggcggcgg cggcggcggc ggcggcagcg     120 gcggggtcg gggggagcg ctccagccgg ccagccccgt ccgtggcgcc cgagccggac      180
ggctgccccg tgtgcgtttg gcggcagcac agccgcgagc tgcgcctaga gagcatcaag     240
tcgcagatct tgagcaaact gcggctcaag gaggcgccca catcagccg cgaggtggtg      300 aagcagctgc tgcccaaggc gccgccgctg cagcagatcc tggacctaca cgacttccag     360
ggcgacgcgc tgcagcccga ggacttcctg gaggaggacg agtaccacgc caccaccgag     420
accgtcatta gcatggccca ggagacggac ccagcagtac agacagatgg cagccctctc     480
tgctgccatt ttcacttcag ccccaaggtg atgttcacaa aggtactgaa ggcccagctg     540
tgggtgtacc tacggcctgt accccgccca gccacagtct acctgcagat cttgcgacta     600
aaacccctaa ctgggggaag gaccgcaggg ggaggggggg aggccggcg tcacatccgt      660 atccgctcac tgaagattga gctgcactca cgctcaggcc attggcagag catcgacttc     720
aagcaagtgc tacacagctg gttccgccag ccacagagca actggggcat cgagatcaac     780
gcctttgatc ccagtggcac agacctggct gtcacctccc tggggccggg agccgagggg     840
ctgcatccat tcatggagct tcgagtccta gagaacacaa acgttcccg gcggaacctg     900 ggtctggact gcgacgagca ctcaagcgag tcccgctgct gccgatatcc cctcacagtg     960
gactttgagg ctttcggctg ggactggatc atcgcaccta gcgctacaa ggccaactac    1020 tgctccggcc agtgcgagta catgttcatg caaaaatatc cgcatacca tttggtgcag    1080 caggccaatc caagaggctc tgctgggccc tgttgtaccc ccaccaagat gtccccaatc    1140
aacatgctct acttcaatga caagcagcag attatctacg gcaagatccc tggcatggtg    1200
gtggatcgct gtggctgctc t                                              1221

<210> SEQ ID NO 9
<211> LENGTH: 109
<212> TYPE: PRT
<213> ORGANISM: Homo sapiens

<400> SEQUENCE: 9

Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Gln Cys Glu
```

```
                35                  40                  45
Tyr Met Phe Met Gln Lys Tyr Pro His Thr His Leu Val Gln Gln Ala
         50                  55                  60

Asn Pro Arg Gly Ser Ala Gly Pro Cys Cys Thr Pro Thr Lys Met Ser
 65                  70                  75                  80

Pro Ile Asn Met Leu Tyr Phe Asn Asp Lys Gln Gln Ile Ile Tyr Gly
                 85                  90                  95

Lys Ile Pro Gly Met Val Val Asp Arg Cys Gly Cys Ser
                100                 105
```

<210> SEQ ID NO 10
<211> LENGTH: 327
<212> TYPE: DNA
<213> ORGANISM: Homo sapiens

<400> SEQUENCE: 10

```
aacctgggtc tggactgcga cgagcactca agcgagtccc gctgctgccg atatcccctc     60
acagtggact ttgaggcttt cggctgggac tggatcatcg cacctaagcg ctacaaggcc    120
aactactgct ccggccagtg cgagtacatg ttcatgcaaa atatccgca tacccatttg     180
gtgcagcagg ccaatccaag aggctctgct gggccctgtt gtaccccccac caagatgtcc   240
ccaatcaaca tgctctactt caatgacaag cagcagatta tctacggcaa gatccctggc   300
atggtggtgg atcgctgtgg ctgctct                                         327
```

<210> SEQ ID NO 11
<211> LENGTH: 274
<212> TYPE: PRT
<213> ORGANISM: Homo sapiens

<400> SEQUENCE: 11

```
Ala Glu Gly Pro Ala Ala Ala Ala Ala Ala Ala Ala Ala Ala Ala Ala
 1               5                  10                  15

Ala Gly Val Gly Gly Glu Arg Ser Ser Arg Pro Ala Pro Ser Val Ala
                 20                  25                  30

Pro Glu Pro Asp Gly Cys Pro Val Cys Val Trp Arg Gln His Ser Arg
             35                  40                  45

Glu Leu Arg Leu Glu Ser Ile Lys Ser Gln Ile Leu Ser Lys Leu Arg
         50                  55                  60

Leu Lys Glu Ala Pro Asn Ile Ser Arg Glu Val Val Lys Gln Leu Leu
 65                  70                  75                  80

Pro Lys Ala Pro Pro Leu Gln Gln Ile Leu Asp Leu His Asp Phe Gln
                 85                  90                  95

Gly Asp Ala Leu Gln Pro Glu Asp Phe Leu Glu Glu Asp Glu Tyr His
                100                 105                 110

Ala Thr Thr Glu Thr Val Ile Ser Met Ala Gln Glu Thr Asp Pro Ala
            115                 120                 125

Val Gln Thr Asp Gly Ser Pro Leu Cys Cys His Phe His Phe Ser Pro
        130                 135                 140

Lys Val Met Phe Thr Lys Val Leu Lys Ala Gln Leu Trp Val Tyr Leu
145                 150                 155                 160

Arg Pro Val Pro Arg Pro Ala Thr Val Tyr Leu Gln Ile Leu Arg Leu
                165                 170                 175

Lys Pro Leu Thr Gly Glu Gly Thr Ala Gly Gly Gly Gly Gly Arg
            180                 185                 190

Arg His Ile Arg Ile Arg Ser Leu Lys Ile Glu Leu His Ser Arg Ser
```

195                     200                     205
             Gly His Trp Gln Ser Ile Asp Phe Lys Gln Val Leu His Ser Trp Phe
                 210                     215                     220
             Arg Gln Pro Gln Ser Asn Trp Gly Ile Glu Ile Asn Ala Phe Asp Pro
             225                     230                     235                     240
             Ser Gly Thr Asp Leu Ala Val Thr Ser Leu Gly Pro Gly Ala Glu Gly
                             245                     250                     255
             Leu His Pro Phe Met Glu Leu Arg Val Leu Glu Asn Thr Lys Arg Ser
                         260                     265                     270
             Arg Arg

<210> SEQ ID NO 12
<211> LENGTH: 822
<212> TYPE: DNA
<213> ORGANISM: Homo sapiens

<400> SEQUENCE: 12
gccgagggcc ccgcggcggc ggcggcggcg gcggcggcgg cggcagcggc gggggtcggg      60
ggggagcgct ccagccggcc agcccgtcc gtggcgcccg agccgacgg ctgccccgtg      120 tgcgtttggc ggcagcacag ccgcgagctg cgcctagaga gcatcaagtc gcagatcttg      180
agcaaactgc ggctcaagga ggcgcccaac atcagccgcg aggtggtgaa gcagctgctg      240
cccaaggcgc cgccgctgca gcagatcctg gacctacacg acttccaggg cgacgcgctg      300
cagcccgagg acttcctgga ggaggacgag taccacgcca ccaccgagac cgtcattagc      360
atggcccagg agacggaccc agcagtacag acagatggca gccctctctg ctgccatttt      420
cacttcagcc ccaaggtgat gttcacaaag gtactgaagg cccagctgtg ggtgtaccta      480
cggcctgtac cccgcccagc cacagtctac ctgcagatct tgcgactaaa accctaact      540 ggggaaggga ccgcaggggg aggggcggga ggccggcgtc acatccgtat ccgctcactg      600
aagattgagc tgcactcacg ctcaggccat tggcagagca tcgacttcaa gcaagtgcta      660
cacagctggt tccgccagcc acagagcaac tggggcatcg agatcaacgc ctttgatccc      720
agtggcacag acctggctgt cacctccctg gggccgggag ccgaggggct gcatccattc      780
atggagcttc gagtcctaga gaacacaaaa cgttcccggc gg                         822

<210> SEQ ID NO 13
<211> LENGTH: 23
<212> TYPE: PRT
<213> ORGANISM: Homo sapiens

<400> SEQUENCE: 13

Met Gln Lys Leu Gln Leu Cys Val Tyr Ile Tyr Leu Phe Met Leu Ile
1               5                   10                  15

Val Ala Gly Pro Val Asp Leu
            20

<210> SEQ ID NO 14
<211> LENGTH: 24
<212> TYPE: PRT
<213> ORGANISM: Homo sapiens

<400> SEQUENCE: 14

Met Val Leu Ala Ala Pro Leu Leu Leu Gly Phe Leu Leu Leu Ala Leu
1               5                   10                  15

Glu Leu Arg Pro Arg Gly Glu Ala
            20

<210> SEQ ID NO 15
<211> LENGTH: 232
<212> TYPE: PRT
<213> ORGANISM: Homo sapiens

<400> SEQUENCE: 15

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 16
<211> LENGTH: 227
<212> TYPE: PRT
<213> ORGANISM: Homo sapiens

<400> SEQUENCE: 16

```
Asp Lys Thr His Thr Cys Pro Pro Cys Pro Ala Pro Glu Ala Leu Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```